United States Patent [19]
Kirsch et al.

[11] Patent Number: 5,968,410
[45] Date of Patent: Oct. 19, 1999

[54] FLUOROCYCLOHEXANE DERIVATIVES, AND LIQUID-CRYSTALLINE MEDIUM

[75] Inventors: Peer Kirsch, Darmstadt; Joachim Krause, Dieburg; Kazuaki Tarumi, Seeheim-Jugenheim, all of Germany

[73] Assignee: Merck Patent Gesellschaft mit Beschrankter Haftung, Germany

[21] Appl. No.: 09/124,216

[22] Filed: Jul. 29, 1998

[30] Foreign Application Priority Data

Jul. 30, 1997 [DE] Germany .......................... 197 32 772

[51] Int. Cl.⁶ .......................... C09K 19/34; C09K 19/32; C09K 19/30; C07D 239/02; C07C 25/13
[52] U.S. Cl. .............................. 252/299.61; 252/299.62; 252/252; 252/299.63; 544/303; 570/127; 570/128; 570/129; 570/130; 570/131; 570/214
[58] Field of Search ................... 252/299.61, 299.62, 252/299.63; 570/127, 128, 129, 130, 131, 214; 549/369; 544/303

[56] References Cited

U.S. PATENT DOCUMENTS

| | | | |
|---|---|---|---|
| 4,510,069 | 4/1985 | Eidenschnik et al. | 252/299.61 |
| 5,108,652 | 4/1992 | Eidenschnik et al. | 252/299.63 |
| 5,662,829 | 9/1997 | Buchecker et al. | 252/299.61 |

FOREIGN PATENT DOCUMENTS

| | | |
|---|---|---|
| 0 107 759 | 5/1994 | European Pat. Off. . |
| 5-125002 | 5/1993 | Japan . |
| 5-229979 | 9/1993 | Japan . |

OTHER PUBLICATIONS

Dialog Web Pub. No. 05–229979 (JP 5229979A) Abstract, 1993.

Dialog Web Pub. No. 05–125002 (JP 5125002 A) Abstract, 1993.

*Primary Examiner*—Shean C. Wu

[57] ABSTRACT

The invention relates to fluorocyclohexane derivatives of the formula I

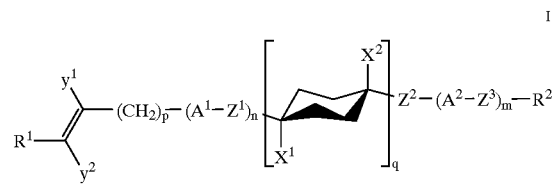

in which $R^1$, $R^2$, $y^1$, $y^2$, $X^1$, $X^2$, $A^1$, $Z^1$, $Z^2$, $Z^3$, n, m, p and q are as defined above.

18 Claims, No Drawings

FLUOROCYCLOHEXANE DERIVATIVES, AND LIQUID-CRYSTALLINE MEDIUM

The invention relates to novel fluorocyclohexane derivatives of the formula I

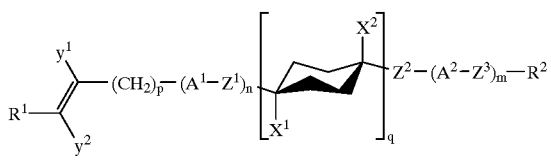

in which $R^1$ is H, F, or an alkyl, alkoxy or alkenyl radical having 1–12 or 2–12 carbon atoms respectively which is unsubstituted, monosubstituted by CN or $CF_3$ or at least monosubstituted by fluorine, e.g., up to perfluoro-substituted by fluorine,

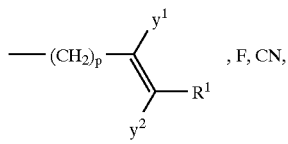, F, CN, an alkyl radical having 1–12 carbon atoms which is unsubstituted, monosubstituted by CN or $CF_3$ or at least monosubstituted by fluorine, e.g., up to perfluoro-substituted, where one or more non-adjacent $CH_2$ groups in this radical may also, in each case independently of one another, be replaced by —O—, —S—, —CO—,

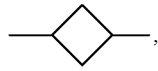

—CO—O—, —O—CO— or —O—CO—O—, $y^1$ and $y^2$, independently of one another, are H or F, $X^1$ and $X^2$ are each, independently of one another, H or F in the axial position, where one of the radicals $X^1$ and $X^2$ on each individual cyclohexane ring substituted by $X^1$ and $X^2$ is F and the other radical is H, $A^1$ and $A^2$ a) are a trans-1,4-cyclohexylene radical, in which, in addition, one or more non-adjacent $CH_2$ groups may be replaced by —O— and/or —S—, b) is a 1,4-phenylene radical, in which, in addition, one or two CH groups may be replaced by N, c) is a radical from the group consisting of 1,4-bicyclo[2.2.2] octylene, piperidine-1,4-diyl, naphthalene-2,6-diyl, decahydro-naphthalene-2,6-diyl and 1,2,3,4-tetrahydronaphthalene-2,6-diyl, d) is 1,4-cyclohexenylene, where the radicals a), b) and d) may be substituted by CN, Cl or F, $Z^1$, $Z^2$ and $Z^3$ are each, independently of one another, —CO—O—, —O—CO—, —$CH_2$O—, —O—, —O—$CH_2$—, —$CH_2CH_2$—, —$CF_2CF_2$—, —$CF_2CH_2$—, —$CH_2CF_2$—, —CHFCHF—, —$CHFCF_2$—, —$CF_2CHF$—, —CH=CH—, —C≡C— or a single bond, p is 0 to 9, q is 1, 2, 3 or 4, n and m are 0, 1, 2 or 3, where m+n+q is 2, 3 or 4.

The compounds of the formula I can be used as components of liquid-crystalline media, in particular for displays based on the principle of the twisted cell, the guest-host effect, the effect of deformation of aligned phases (DAP) or electrically controlled birefringence (ECB), or the effect of dynamic scattering. The substances employed hitherto for this purpose all have certain disadvantages, for example inadequate stability to exposure to heat, light or electric fields, or unfavourable elastic and/or dielectric properties.

Compounds containing fluorocyclohexane units are disclosed, for example, in JP 05125002, JP 05229979 and EP 0107759, but no compounds containing alkenyl radicals as terminal substituents are described therein.

The invention had the object of finding novel, stable, liquid-crystalline or mesogenic compounds which are suitable as components of liquid-crystalline media, in particular for TFT and STN displays.

It has now been found that the compounds of the formula I are eminently suitable as components of liquid-crystalline media. They can be used to obtain stable liquid-crystalline media, particularly suitable for TFT or STN displays. The novel compounds are distinguished, in particular, by high thermal stability, which is advantageous for a high holding ratio, and exhibit favourable clearing points at the same time as comparatively low rotational viscosity values. The compounds of the formula I have highly negative dielectric anisotropy and are therefore particularly suitable for displays based on the effect of deformation of aligned phases.

In addition, the provision of compounds of the formula I very generally considerably broadens the range of liquid-crystalline substances which are suitable from various applicational points of view for the preparation of liquid-crystalline mixtures.

The compounds of the formula I have a broad range of applications. Depending on the choice of substituents, these compounds can be used as base materials of which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or to optimize its threshold voltage and/or its viscosity. The definition of the formula I includes all isotopes of the chemical elements which occur in the compounds of the formula I.

In the pure state, the compounds of the formula I are colourless and form liquid-crystalline mesophases in a temperature range which is favourably located for electro-optical use. They are stable chemically, thermally and to light.

The invention thus relates to the compounds of the formula I and to the use of these compounds as components of liquid-crystalline media. The invention furthermore relates to liquid-crystalline media containing at least one compound of the formula I, and to liquid-crystal display elements, in particular electro-optical display elements, which contain media of this type.

Above and below, $R^1$, $R^2$, $y^1$, $y^2$, $X^1$, $X^2$, $A^1$, $A^2$, $Z^1$, $Z^2$, $Z^3$, p, q, n and m are as defined above, unless expressly stated otherwise.

For reasons of simplicity, Cyc below denotes a 1,4-cyclohexylene radical, Che denotes a 1,4-cyclo-hexenylene radical, Dio denotes a 1,3-dioxane-2,5-diyl radical, Dit denotes a 1,3-dithiane-2,5-diyl radical, Phe denotes a 1,4- phenylene radical, Pyd denotes a pyridine-2,5-diyl radical, Pyr denotes a pyrimidine-2,5-diyl radical and Bco denotes a bicyclo[2.2.2]-octylene radical, where Cyc and/or Phe may be unsubstituted or monosubstituted or polysubstituted by Cl, F or CN.

W denotes the following structural unit:

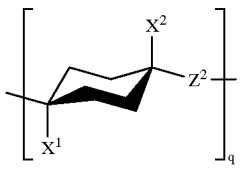

while $R^a$ is the following radical:

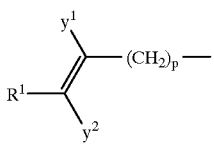

in which $X^1$, $X^2$, $Z^2$, $y^1$, $y^2$, $R^1$, p and q are as defined above.

The formula I covers compounds of the subformula Ia:

$R^a$-W-$R^2$      Ia compounds of the subformulae Ib, Ic and Id:

$R^a$-W-$A^2$-$R^2$      Ib

R-W-$Z^2$-$A^2$-$R^2$      Ic $R^a$-$A^1$-$Z^1$-W-$R^2$      Id compounds of the subformulae Ie to Ii:

$R^a$-W-$A^2$-$A^2$-$R^2$      Ie $R^a$-W-$A^2$-$Z^2$-$A^2$-$R^2$      If $R^a$-W-$Z^2$-$A^2$-$A^2$-$R^2$      Ig $R^a$-W-$Z^2$-$A^2$-$Z^2$-$A^2R^2$      Ih $R^a$-$A^1$-$Z^1$-W-$A^2$-$R^2$      Ii and compounds of the subformulae Ij to Ir:

$R^a$-W-$A^2$-$A^2$-$A^2$-$R^2$      Ij $R^a$-W-$Z^2$-$A^2$-$A^2$-$A^2$-$R^2$      Ik $R^a$-W-$A^2$-$Z^2$-$A^2$-$A^2$-$R^2$      Il $R^a$-W-$A^2$-$A^2$-$Z^2$-$A^2$-$R^2$      Im $R^a$-W-$Z^2$-$A^2$-$Z^2$-$A^2$-$A^2$-$R^2$      In $R^a$-W-$Z^2$-$A^2$-$A^2$-$Z^2$-$A^2$-$R^2$      Io $R^a$-W-$A^2$-$Z^2$-$A^2$-$Z^2$-$A^2$-$R^2$      Ip $R^a$-W-$Z^2$-$A^2$-$Z^2$-$A^2$-$Z^2$-$A^2$-$R^2$      Iq $R^a$-$A^1$-$Z^1$-W-$A^2$-$Z^2$-$A^2R^2$      Ir.

Of these, particular preference is given to those of the subformulae Ia, Ib, Id, Ie, If, Ih, Ii and Ij.

The preferred compounds of the subformula Ib include those of the subformulae Iba and Ibb:

$R^a$-W-Phe-$R^2$      Iba $R^a$-W-Cyc-$R^2$      Ibb.

The preferred compounds of the subformula Ic include those of the subformulae Ica and Icb:

$R^a$-W-$Z^2$-Phe-$R^2$      Ica $R^a$-W-$Z^2$-Cyc-$R^2$      Icb.

The preferred compounds of the subformula Id include those of the subformulae Ida and Idb:

$R^a$-Dio-$Z^1$-W-$R^2$      Ida $R^a$-CYC-$Z^1$-W-$R^2$      Idb.

The preferred compounds of the subformula Ie include those of the subformulae Iea to Ieg:

$R^a$-W-Cyc-CyC-$R^2$      Iea $R^a$-W-Cyc-Phe-$R^2$      Ieb $R^a$-W-Phe-Phe-$R^2$      Iec $R^a$-W-Pyd-Phe-$R^2$      Ied $R^a$-W-Phe-Cyc-$R^2$      Iee $R^a$-W-Dio-Phe-$R^2$      Ief $R^a$-W-Pyr-Phe-$R^2$      Ieg.

Of these, those of the formulae Iea, Ieb, Iec and Iee are particularly preferred.

The preferred compounds of the subformula If include those of the subformulae Ifa to Ifg:

$R^a$-W-CyC-$Z^2$-Cyc-$R^2$      Ifa $R^a$-W-Cyc-$Z^2$-Dio-$R^2$      Ifb $R^a$-W-Phe-$Z^2$-Phe-$R^2$      Ifc $R^a$-W-Pyr-$Z^2$-Phe-$R^2$      Ifd $R^a$-W-Pyd-$Z^2$-Phe-$R^2$      Ife $R^a$-W-Cyc-$CH_2$-$CH_2$-Cyc-$R^2$      Iff $R^a$-W-$A^2$-$CH_2CH_2$-Phe-$R^2$      Ifg.

The preferred compounds of the subformula Ig include those of the subformulae Iga to Igh:

$R^a$-W-$Z^2$-Cyc-Cyc-$R^2$      Iga $R^a$-W-$CH_2CH_2$-$A^2$-$A^2$-$R^2$      Igb $R^a$-W-$Z^2$-Cyc-Phe-$R^2$      Igc $R^a$-W-OCO-$A^2$-Phe-$R^2$      Igd $R^a$-W-$Z^2$-Phe-Phe-$R^2$      Ige $R^a$-W-$Z^2$-Pyr-$A^2$-$R^2$      Igf $R^a$-W-$Z^2$-Pyd-$A^2$-$R^2$      Igg $R^a$-W-$Z^2$-Dio-$A^2$-$R^2$      Igh.

Of these, those of the subformulae Iga, Igb, Igc and Ige are particularly preferred.

The preferred compounds of the subformula Ih include those of the subformulae Iha to Ihe:

$R^a$-W-CH$_2$CH$_2$-Phe-Z$^2$-A$^2$R$^2$  Iha $R^a$-W-COO-A$^2$Z$^2$-Phe-R$^2$  Ihb $R^a$-W-Z$^2$-Cyc-Z$^2$-Cyc-R$^2$  Ihc $R^a$-W-Z$^2$-Phe-Z$^2$-Phe-R$^2$  Ihd $R^a$-W-CH$_2$CH$_2$-Cyc-Z$^2$-Cyc-R$^2$  Ihe.

The preferred compounds of the subformula Ii include those of the subformulae Iia to Iie:

$R^a$-CH$_2$CH$_2$-W-Phe-R$^2$  Iia $R^a$-Dio-W-Phe-R$^2$  Iib $R^a$-Phe-W-Cyc-R$^2$  Iic $R^a$-Cyc-W-Cyc-R$^2$  Iid $R^a$-Dio-CH$_2$CH$_2$-W-Cyc-R$^2$  Iie.

The preferred compounds of the subformulae Ij to Ir include those of the subformulae Is to Iz:

$R^a$-W-A$^2$-Cyc-Cyc-R$^2$  Is $R^a$-W-A$^2$-Cyc-Phe-R$^2$  It $R^a$-W-A$^2$-CH$_2$CH$_2$-A$^2$-Phe-R$^2$  Iu $R^a$-W-Z$^2$-Cyc-Z$^2$-A$^2$-Phe-R$^2$  Iv $R^a$-W-Phe-Phe-Phe-R$^2$  Iw $R^a$-W-Phe-Z$^2$A$^2$-Phe-R$^2$  Ix $R^a$-W-A$^2$-Phe-Z$^2$-Phe-R$^2$  Iy $R^a$-W-Z$^2$-Cyc-Z$^2$-Phe-R$^2$  Iz.

A group of preferred compounds of the formula I includes the compounds of the subformulae I1 to I23:

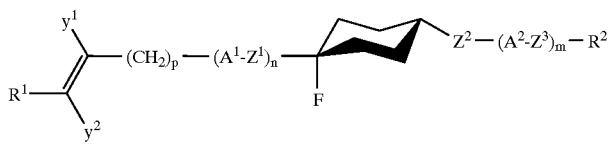

I1

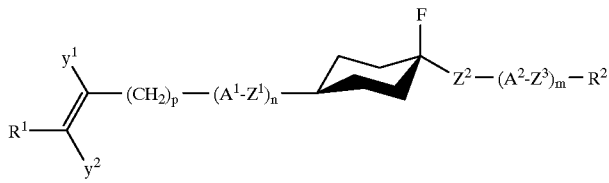

I2

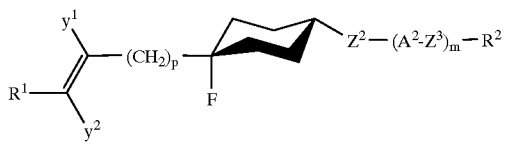

I3

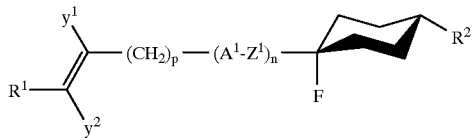

I4

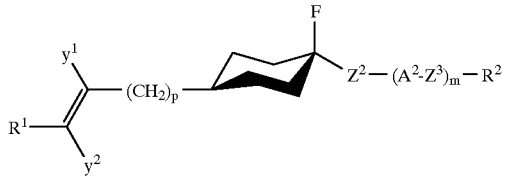

I5

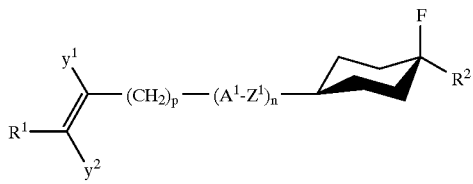

I6

-continued
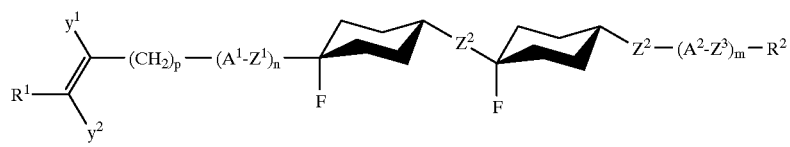
I7
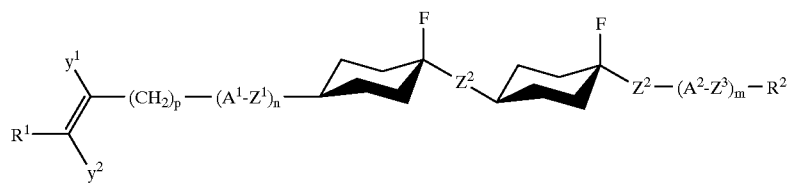
I8
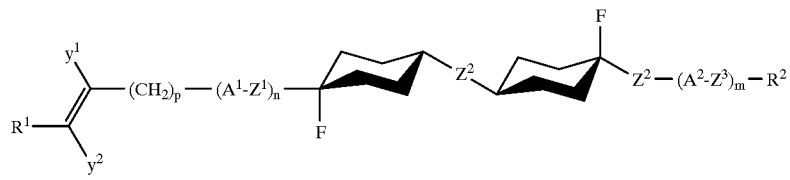
I9
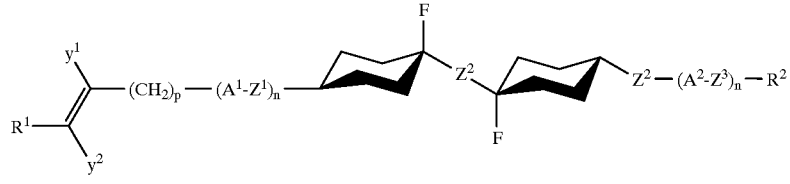
I10
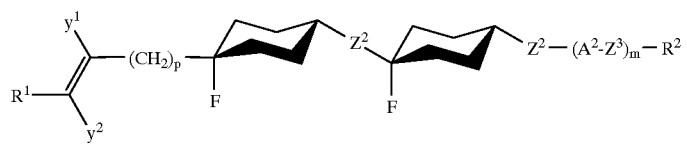
I11
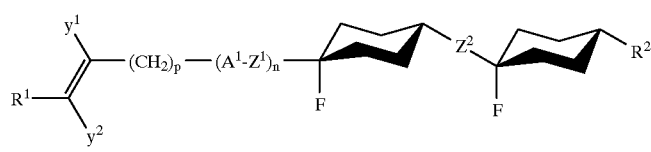
I12
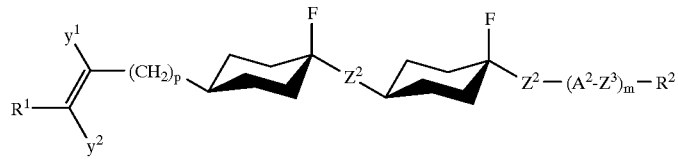
I13
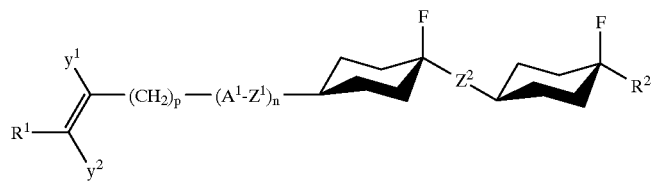
I14
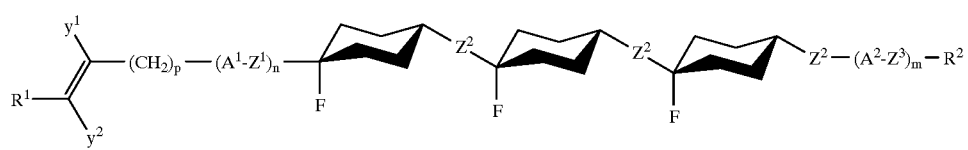
I15

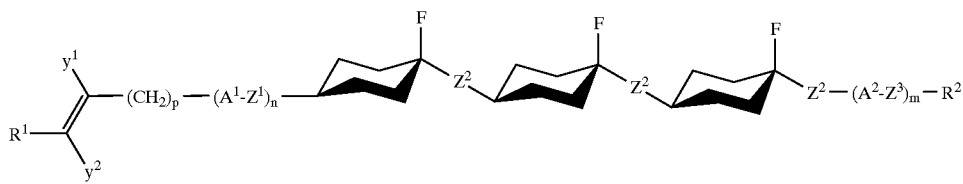
I16
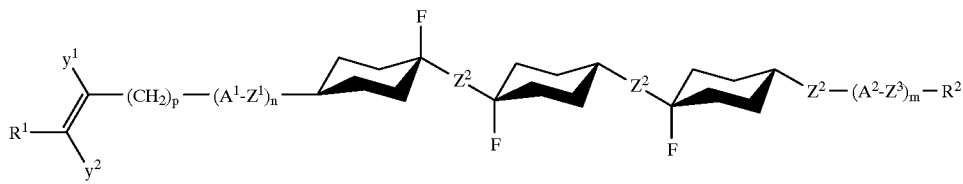
I17
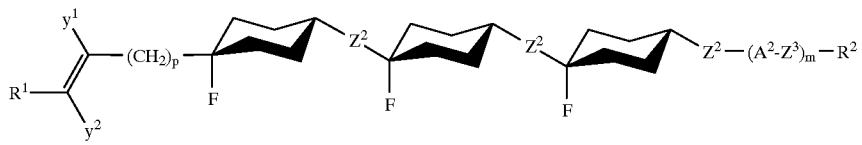
I18
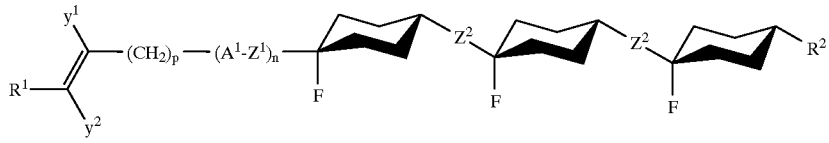
I19
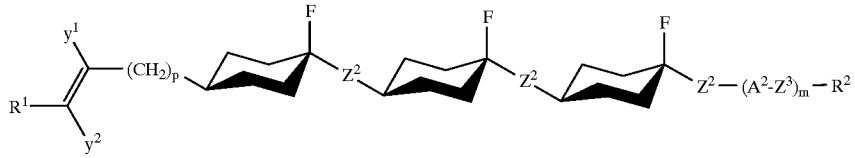
I20
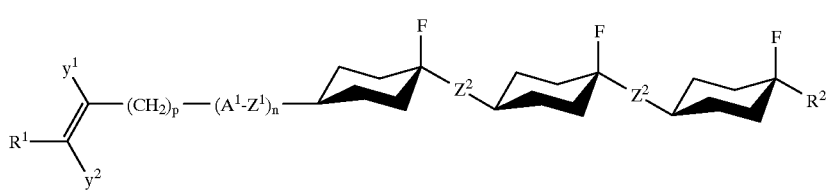
I21
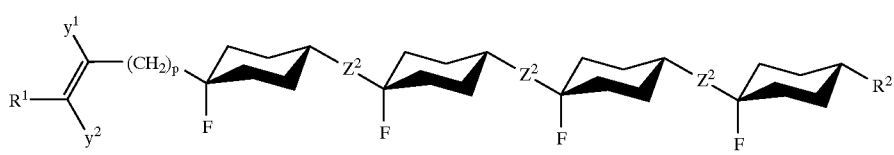
I22
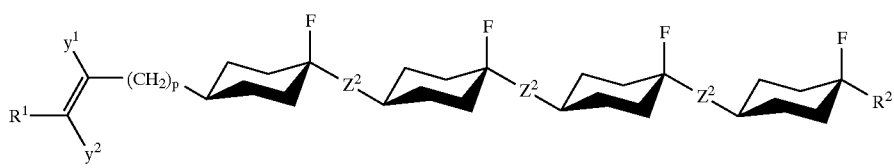
I23
in which $R^1$, $R^2$, $y^1$, $y^2$, $A^1$, $A^2$, $Z^1$, $Z^2$, $Z^3$, n, m and p are as defined above.
In the compounds of the formulae above and below, $R^1$ is preferably H, straight-chain alkyl having 1 to 7 carbon atoms, straight-chain fluoroalkyl having 1 to 7 carbon atoms or F. In particular, $R^1$ is H, straight-chain alkyl having 1 to 3 carbon atoms or $CF_3$.

$R^2$ is preferably

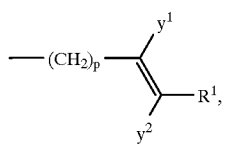

F, —CN, —CF$_3$, —OCF$_3$, —OCHFCF$_3$, —OCF$_2$CF$_3$, straight-chain alkyl or alkoxy having 1 to 10 carbon atoms, or straight-chain fluoroalkyl or fluoroalkoxy having 1 to 10 carbon atoms. $R^2$ is particularly preferably straight-chain alkyl or alkoxy having 1 to 7 carbon atoms, F, —CN, —OCF$_3$ or

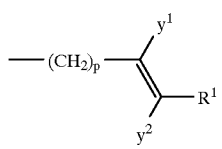

$y^1$ and $y^2$ are preferably H.

p is preferably 0, 1, 2, 3 or 4, in particular 0, 1 or 2, very particularly preferably 1 or 2.

$A^1$ and $A^2$ are preferably Phe, Cyc, Che, Pyd, Pyr or Dio. The compounds of the formula I preferably contain not more than one of the radicals Bco, Pyd, Pyr, Dio and Dit.

If the rings $A^1$ and $A^2$ are present more than once, the rings can have identical or different meanings. The same also applies to the bridges $Z^1$ and $Z^2$, to the substituents $X^1$ and $X^2$, to $y^1$ and $y^2$ and to $R^1$ and p.

Preference is also given to compounds of the formula I and all subformulae in which $A^1$ or $A^2$ is 1,4-phenylene which is monosubstituted or disubstituted by F or CN.

$A^1$ or $A^2$ is preferably

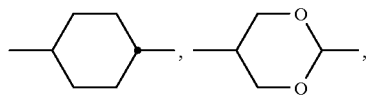

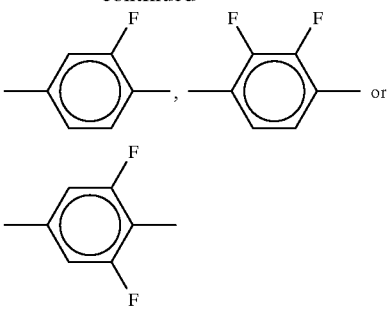

$Z^1$, $Z^2$ and $Z^3$ are, independently of one another, preferably —CH$_2$CH$_2$—, —CF$_2$CF$_2$—, —CH=CH— or a single bond, particularly preferably a single bond, —CH$_2$CH$_2$— or —CF$_2$CF$_2$—. $Z^1$, $Z^2$ and $Z^3$ are very particularly preferably a single bond or —CH$_2$CH$_2$—.

m and n are preferably 0, 1 or 2, in particular 0 or 1.

Compounds of the formula I in which q is 1 or 2 are preferred. Very particular preference is given to compounds of the formula I in which q is 2.

Preference is furthermore given to compounds of the formula I in which $R^1$ is H or straight-chain alkyl having 1 to 3 carbon atoms, and $R^2$ is alkenyl having 2 to 10 carbon atoms.

Particular preference is furthermore given to compounds of the formula I which are characterized in that $R^2$ is straight-chain alkyl or alkoxy having 1 to 10 carbon atoms or alkenyl having 2 to 10 carbon atoms, and $A^1$ or $A^2$ is Cyc.

The 1,4-cyclohexenylene group preferably has the following structures:

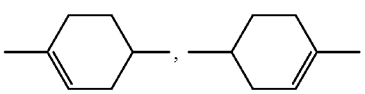

The following group of compounds of the subformulae I24 to I151 represents a further preferred embodiment of the invention:

I24

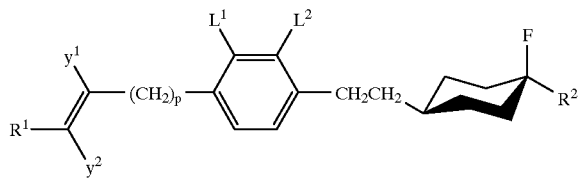

I25

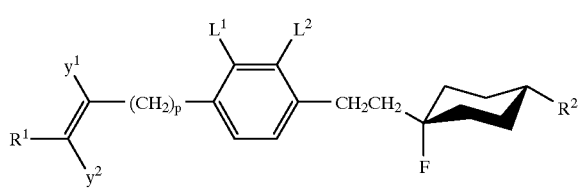

-continued
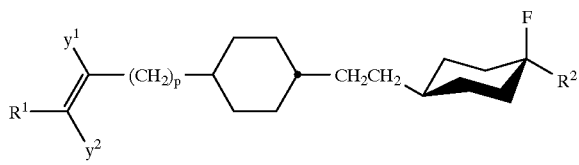
I26
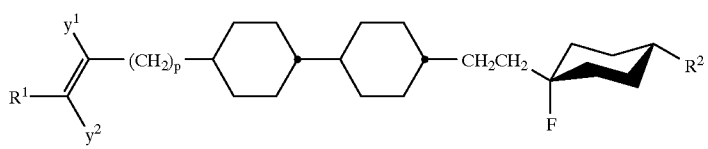
I27
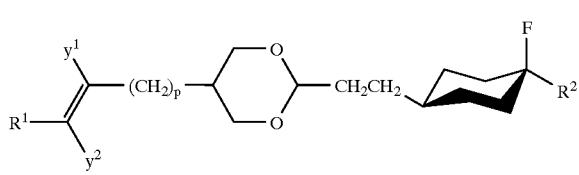
I28
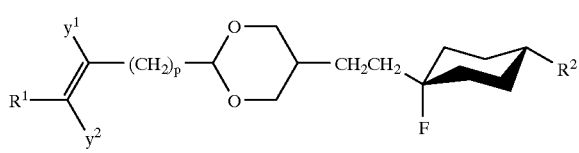
I29
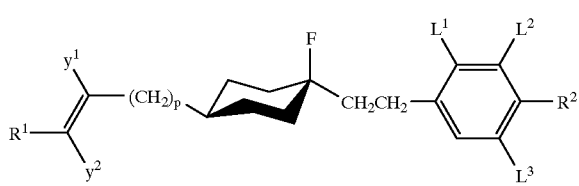
I30
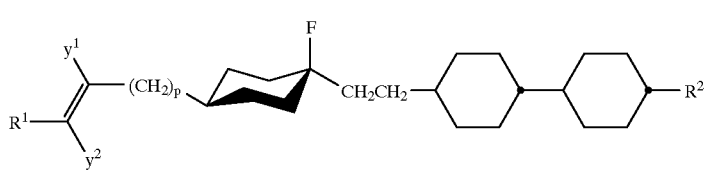
I31
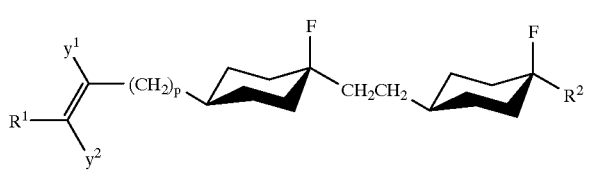
I32
I33
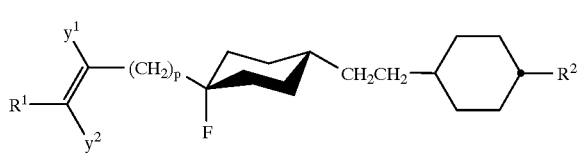
I34

I35
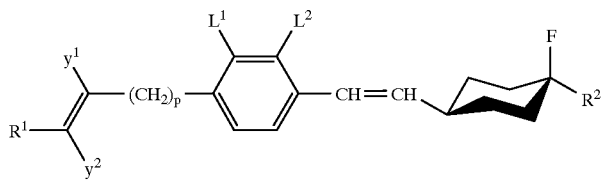
I36
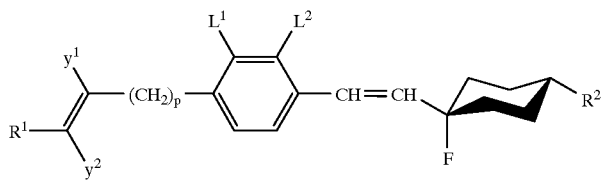
I37
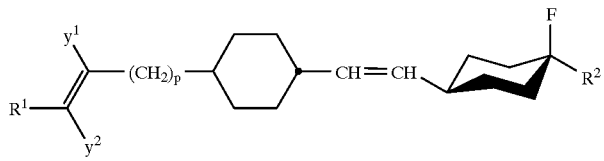
I38
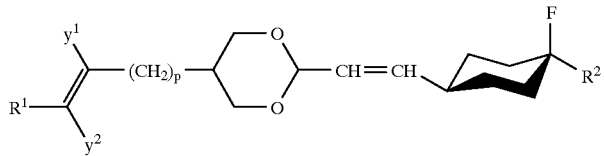
I39
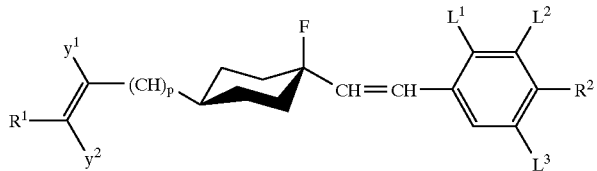
I40
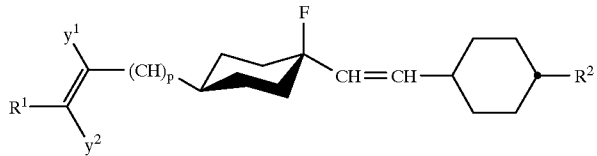
I41
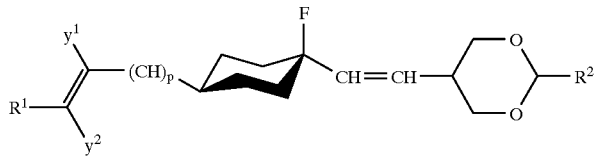
I42
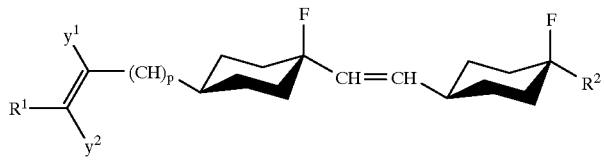
I43

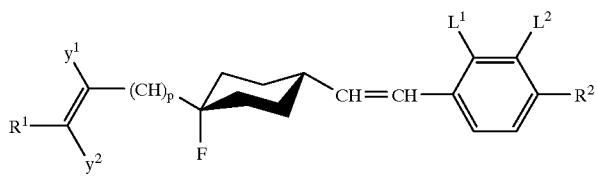
I44
I45
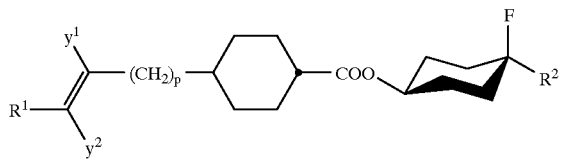
I46
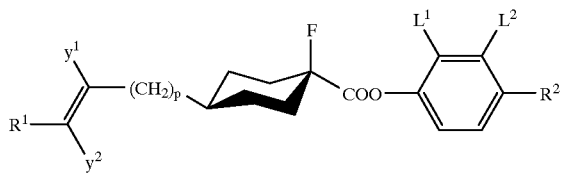
I47
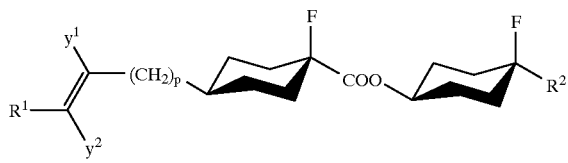
I48
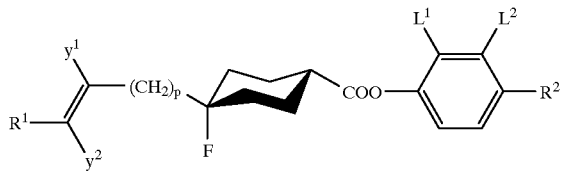
I49
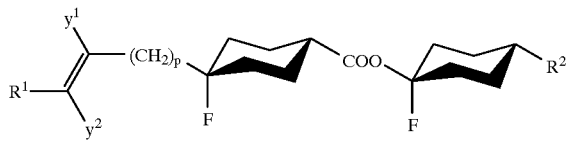
I50
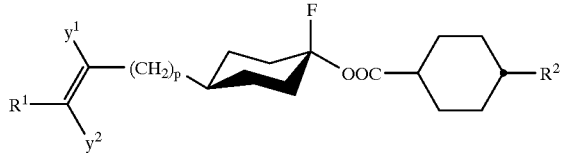
I51
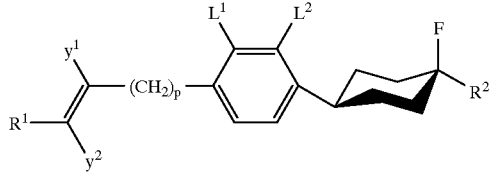
I52

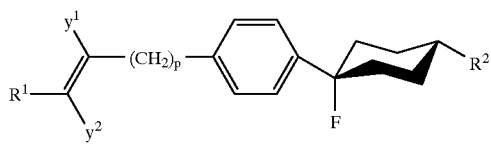
I53
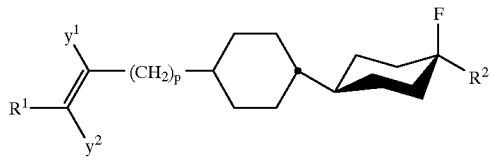
I54
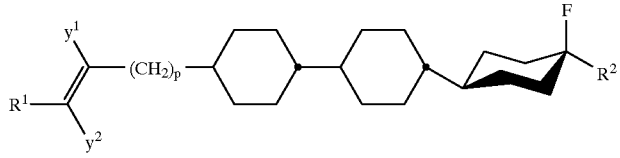
I55
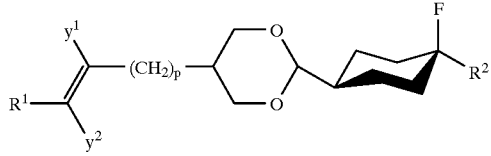
I56
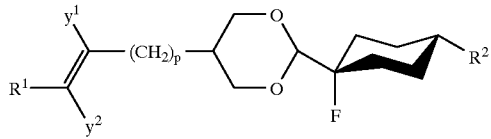
I57
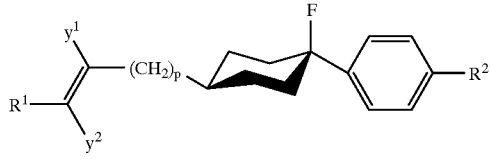
I58
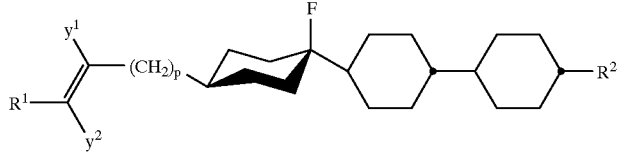
I59
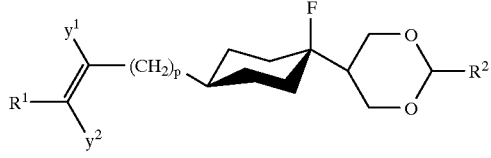
I60
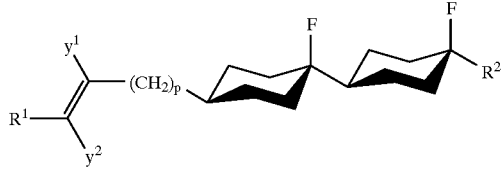
I61

-continued
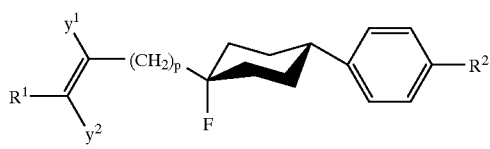
I62
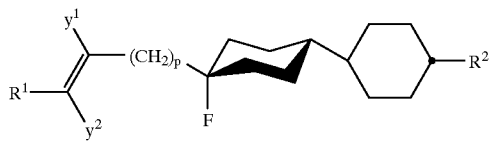
I63
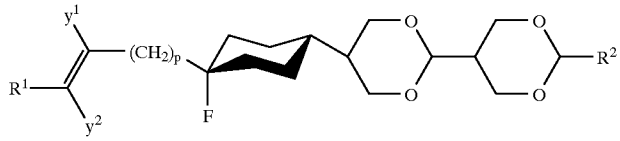
I64
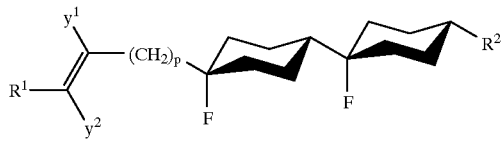
I65
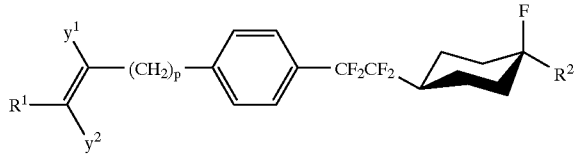
I66
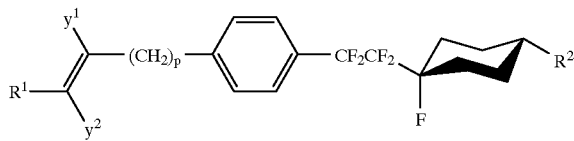
I67
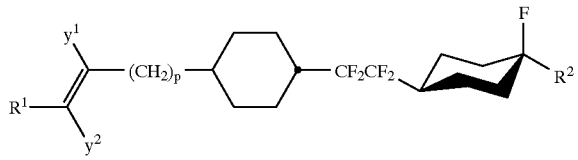
I68
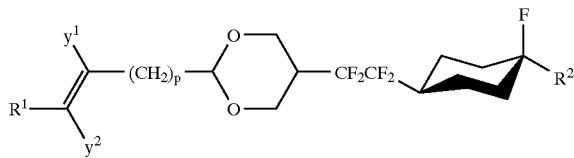
I69
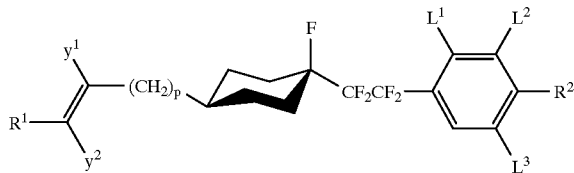
I70

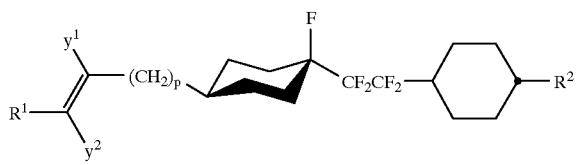 I71
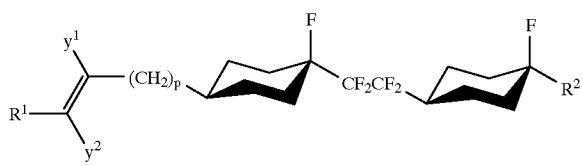 I72
 I73
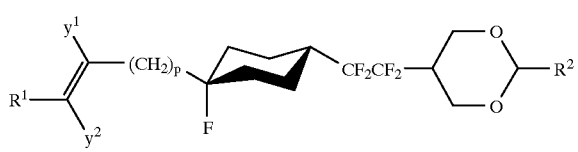 I74
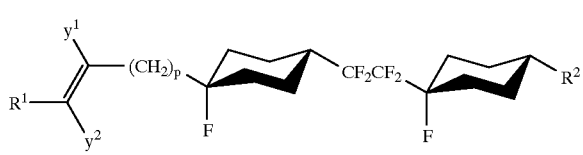 I75
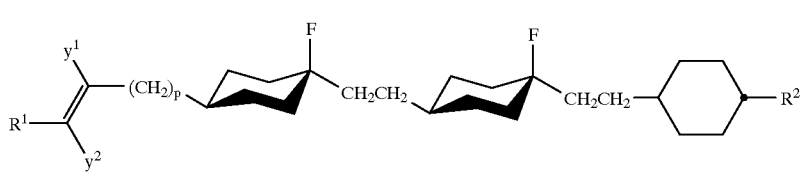 I76
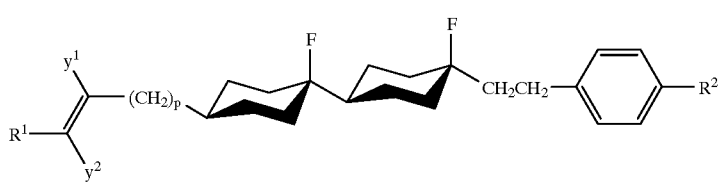 I77
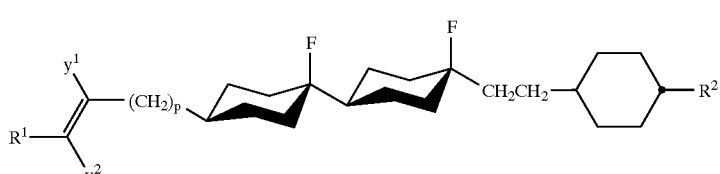 I78
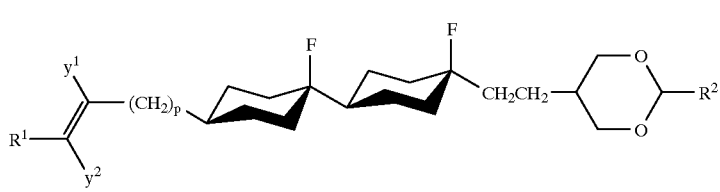 I79

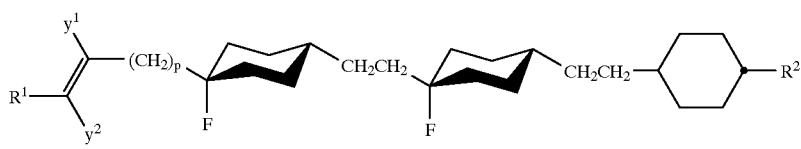
I80
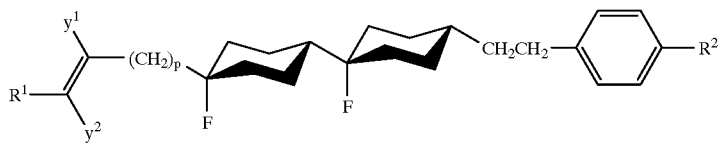
I81
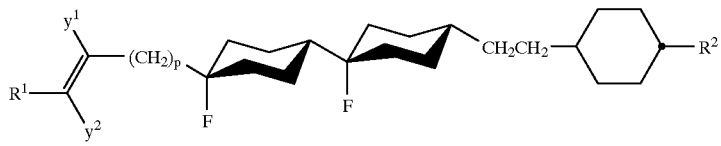
I82
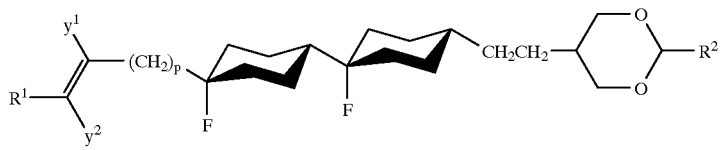
I83
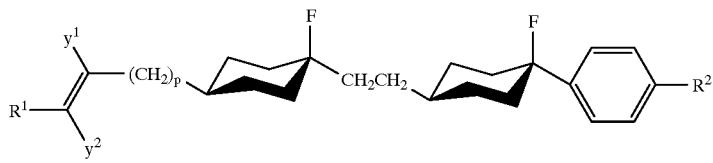
I84
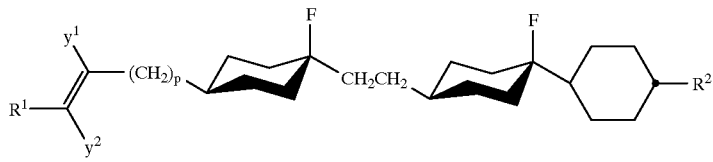
I85
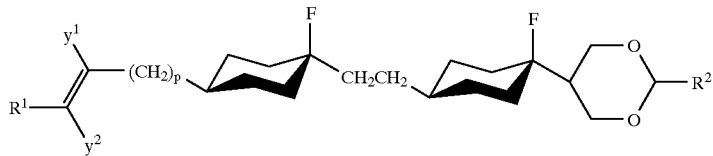
I86
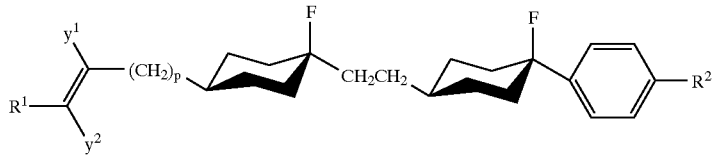
I87
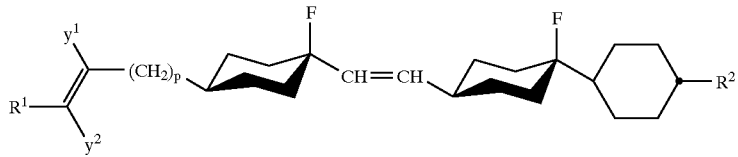
I88

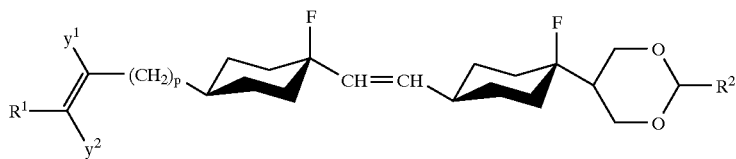
I89
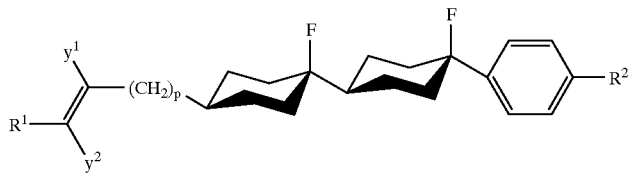
I90
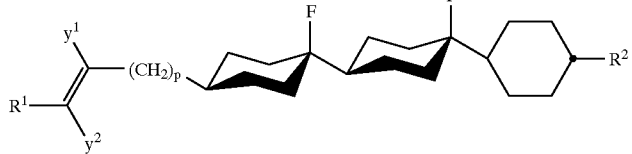
I91
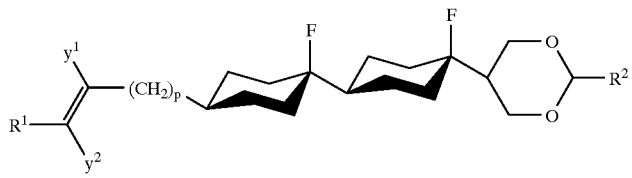
I92
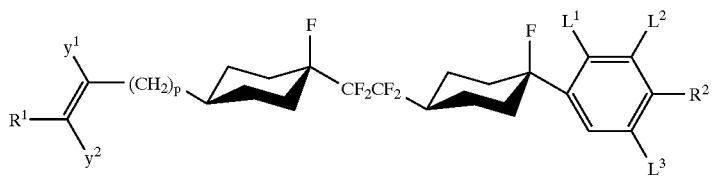
I93
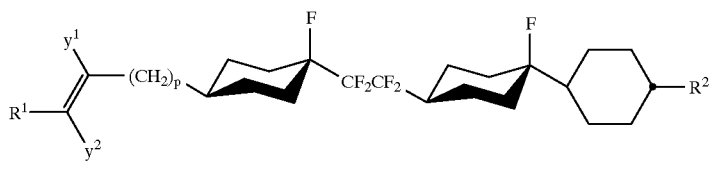
I94
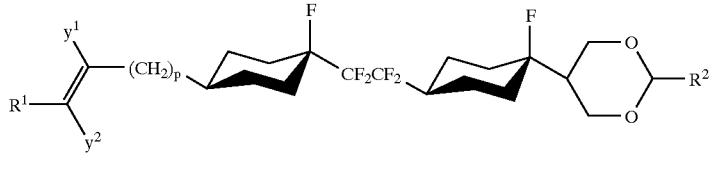
I95
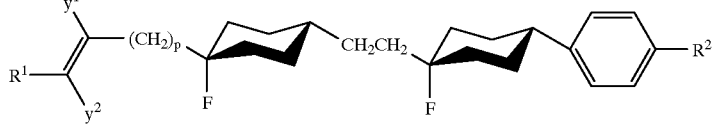
I96
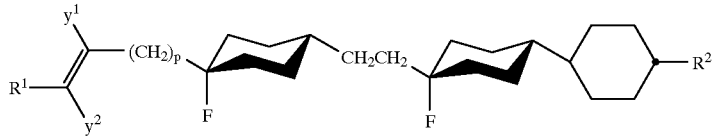
I97

-continued
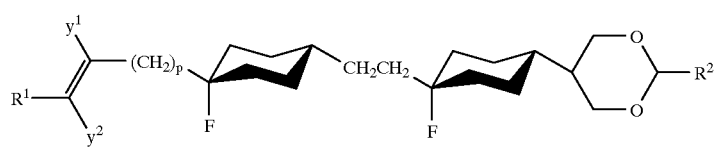
I98
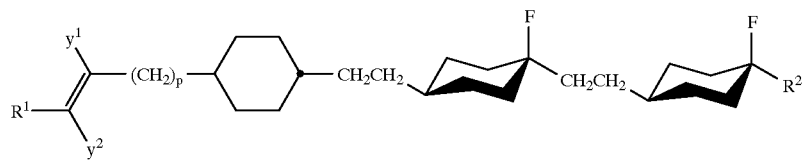
I99
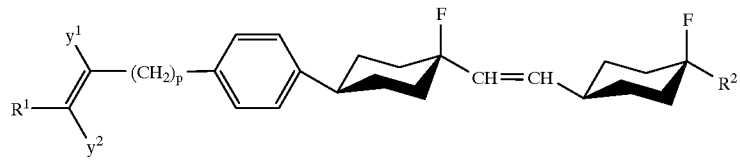
I100
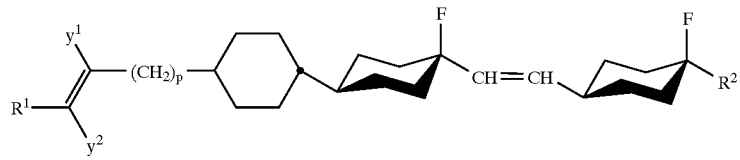
I101
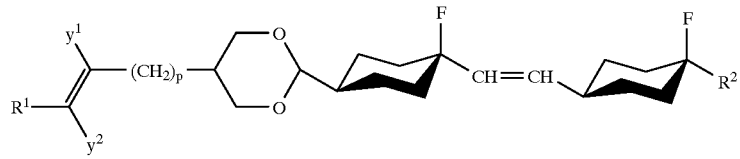
I102
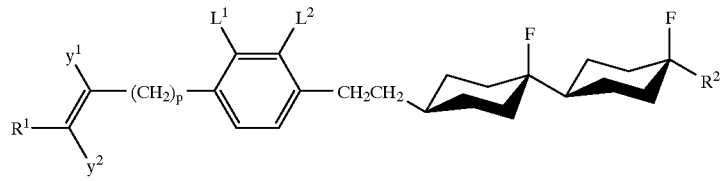
I103
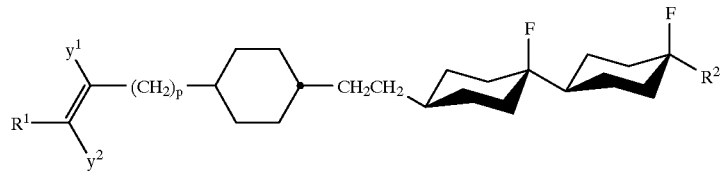
I104
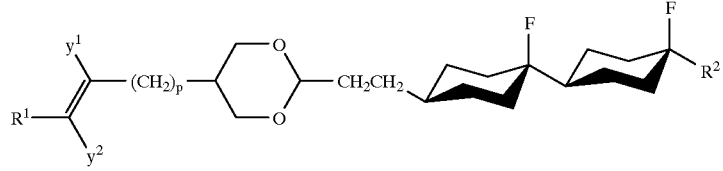
I105
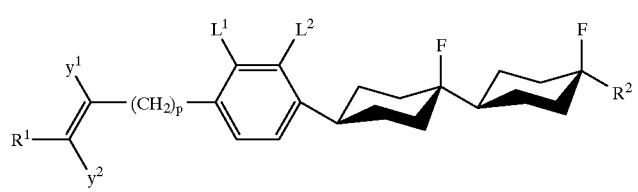
I106

-continued
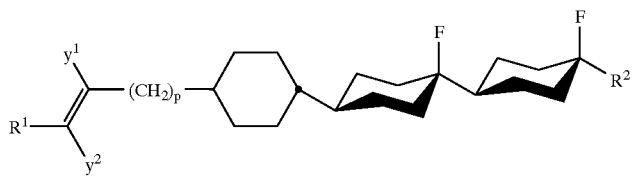 I107
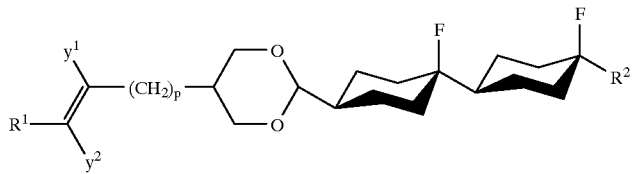 I108
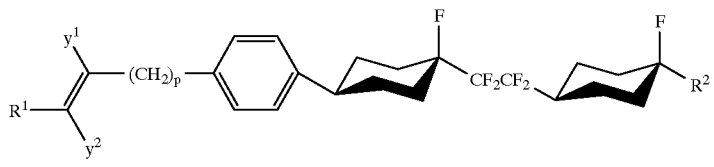 I109
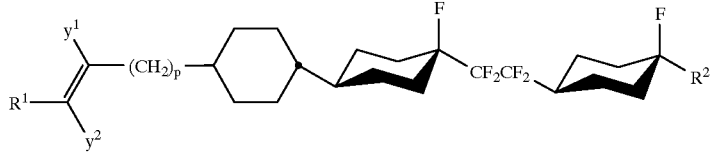 I110
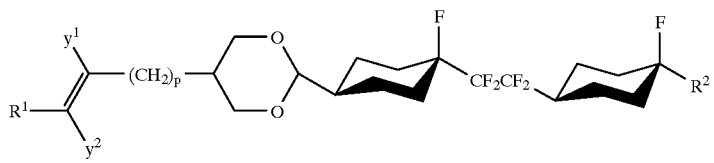 I111
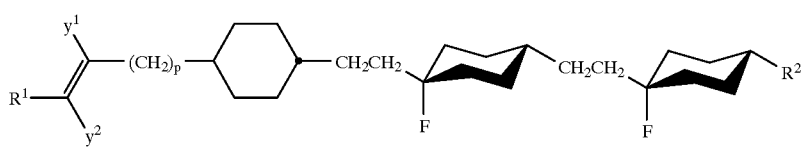 I112
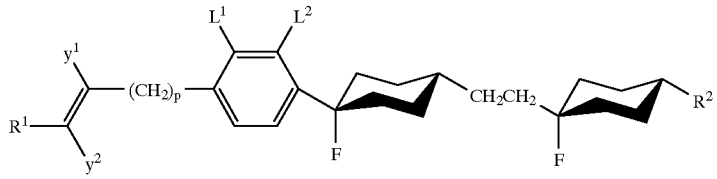 I113
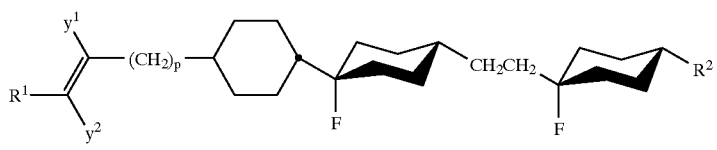 I114
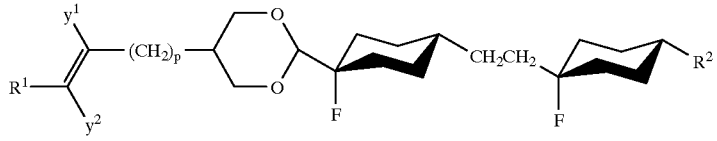 I115

-continued
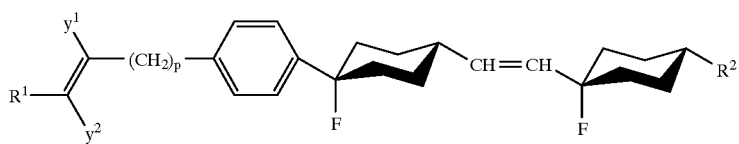 I116
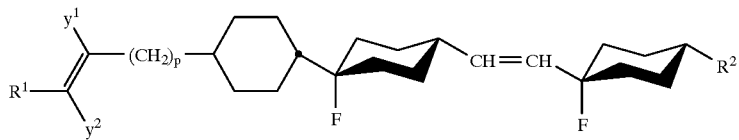 I117
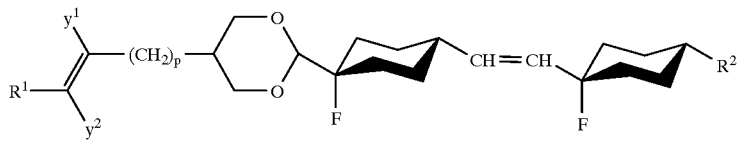 I118
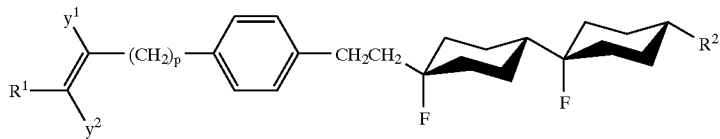 I119
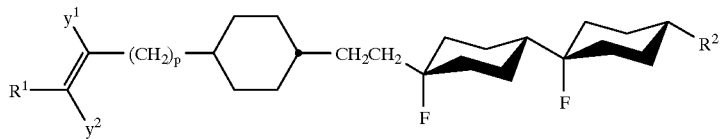 I120
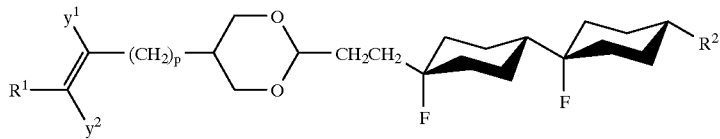 I121
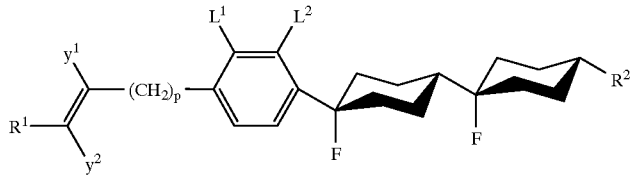 I122
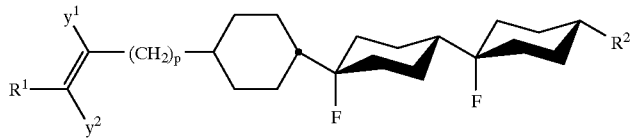 I123
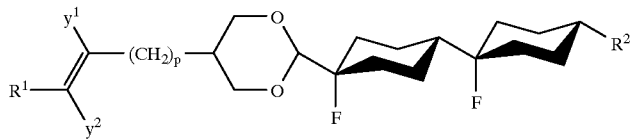 I124
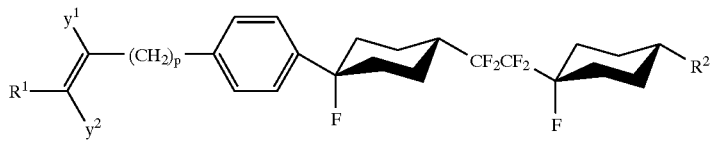 I125

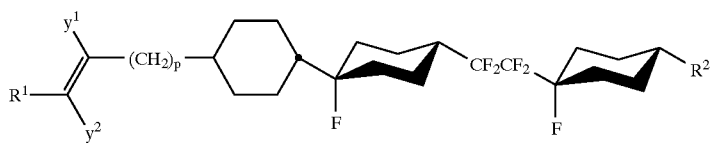
I126
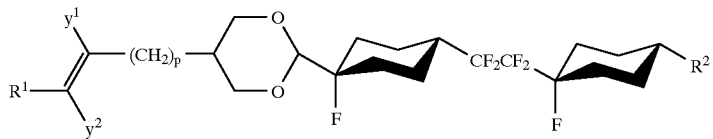
I127
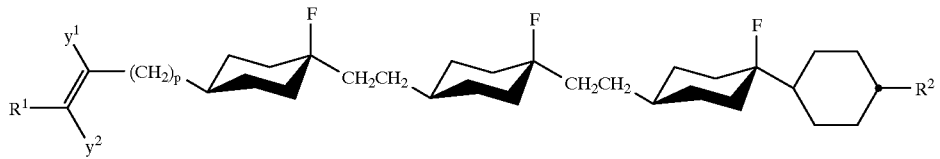
I128
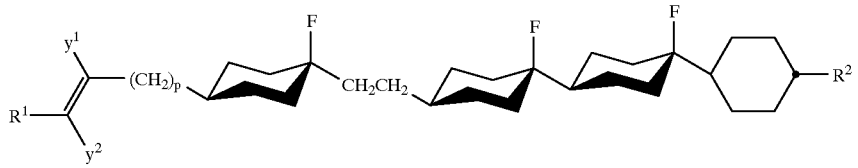
I129
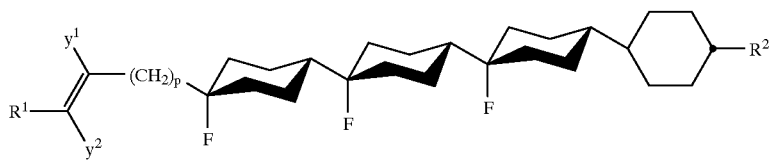
I130
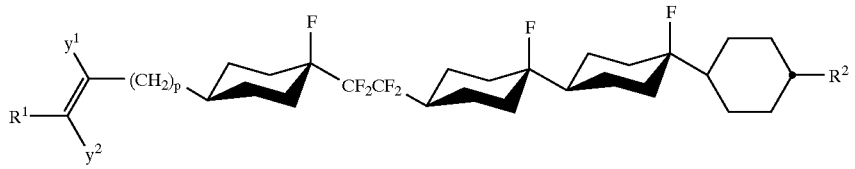
I131
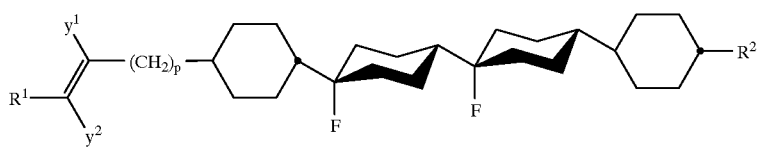
I132
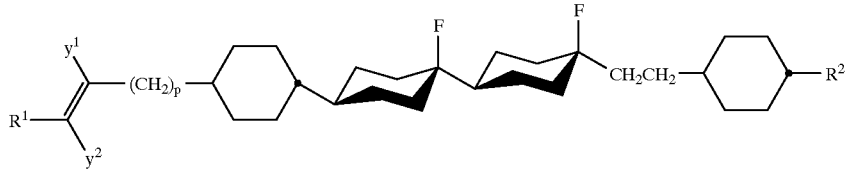
I133
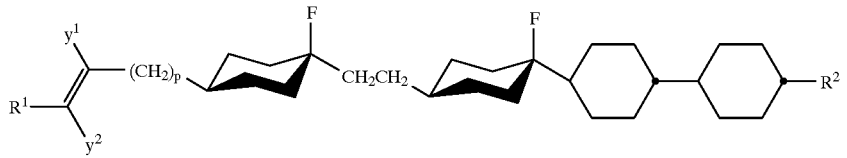
I134

I135
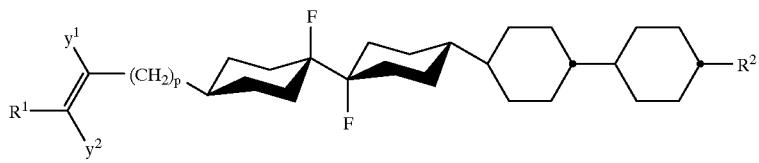
I136
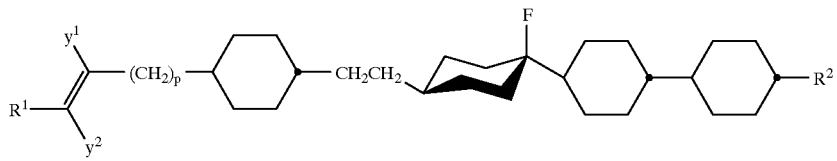
I137
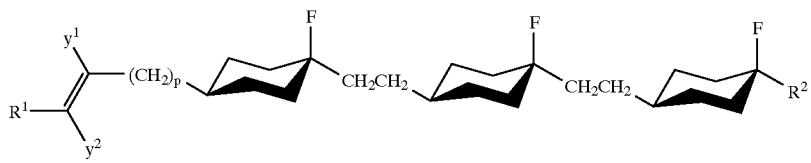
I138
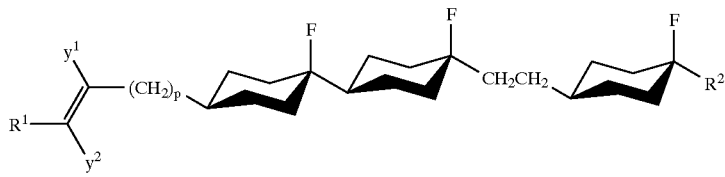
I139
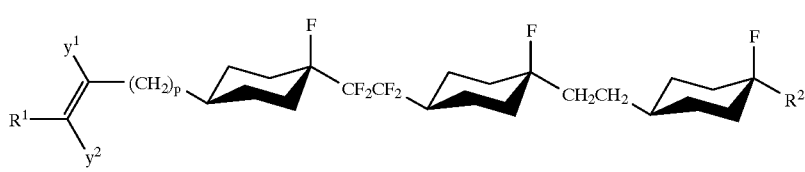
I140
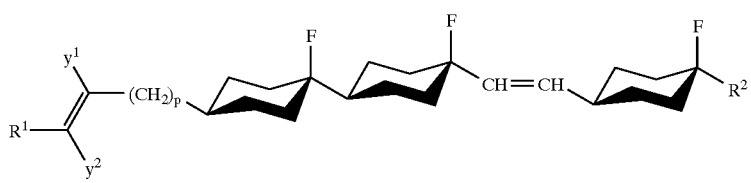
I141
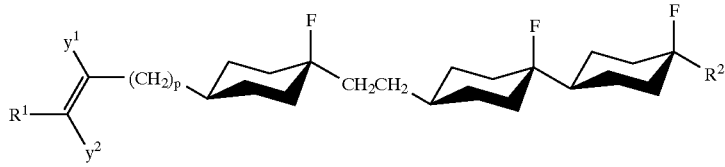
I142
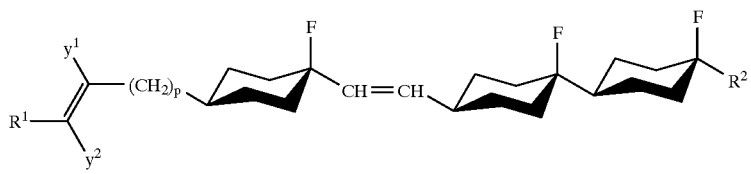

I143
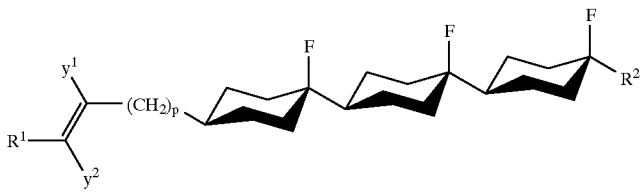
I144
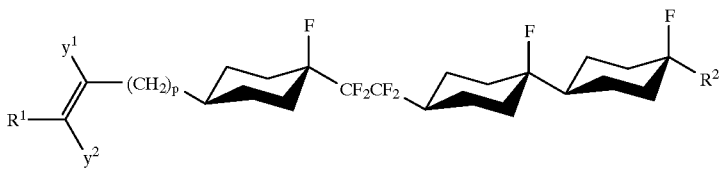
I145
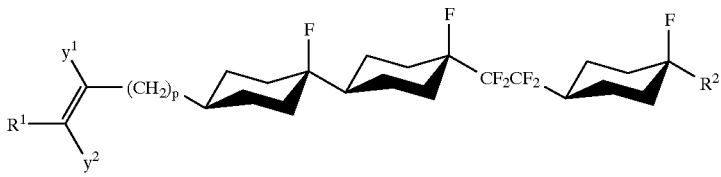
I146
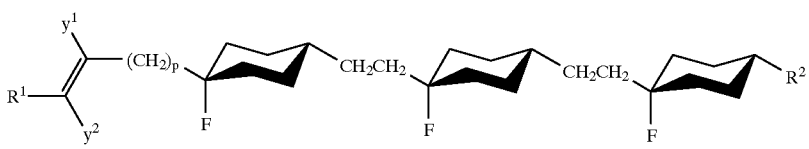
I147
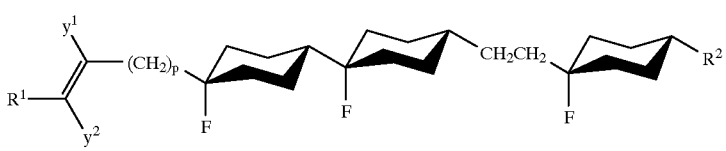
I148
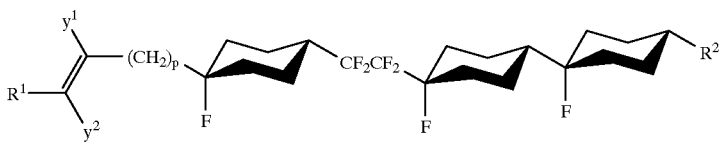
I149
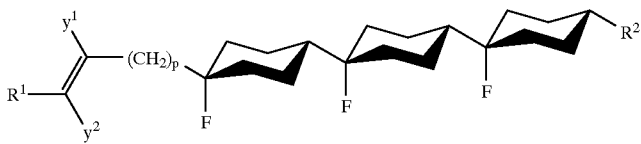
I150
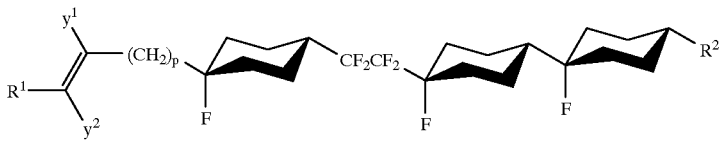
I151
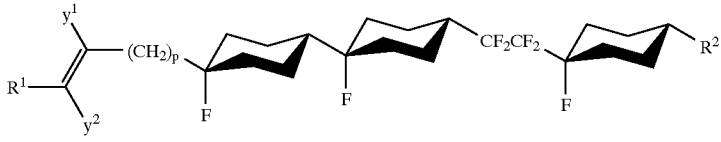
in which $R^1$, $y^1$, $y^2$, p and $R^2$ are as defined above, and $L^1$, $L^2$ and $L^3$, independently of one another, are H or F.
If $R^1$ and/or $R^2$ in the formulae above and below is an alkyl radical and/or alkoxy radical, this can be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentyloxy, hexyloxy or heptyloxy, furthermore methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

Oxaalkyl is preferably straight-chain 2-oxapropyl (=methoxymethyl), 2-(=ethoxymethyl) or 3-oxabutyl (=2-methoxyethyl), 2- , 3- or 4-oxapentyl, 2- , 3- , 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If $R^1$ and/or $R^2$ is an alkyl radical in which one $CH_2$ group has been replaced by —CH=CH—, this can be straight-chain or branched. It is preferably straight-chain and has 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If $R^1$ is an alkyl radical in which one $CH_2$ group has been replaced by —O— and one has been replaced by —CO—, these are preferably adjacent. These thus contain one acyloxy group —CO—O— or one oxycarbonyl group —O—CO—. These are preferably straight-chain and have 2 to 6 carbon atoms. Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If $R^1$ is an alkyl radical in which one $CH_2$ group has been replaced by unsubstituted or substituted —CH=CH— and an adjacent $CH_2$ group has been replaced by CO or CO—O or O—CO—, this can be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl and 9-methacryloyloxynonyl.

If $R^1$ and/or $R^2$ is an alkyl or alkenyl radical which is monosubstituted by CN or $CF_3$, this radical is preferably straight-chain, and the substitution by CN or $CF_3$ is in the ω-position.

If $R^1$ and/or $R^2$ is an alkyl or alkenyl radical which is at least monosubstituted by halogen, this radical is preferably straight-chain, and halogen is preferably F or Cl. In the case of multiple substitution, halogen is preferably F. The resulting radicals also include perfluorinated radicals. In the case of monosubstitution, the fluorine or chlorine substituent can be in any desired position, but is preferably in the ω-position.

Compounds of the formula I containing branched wing groups $R^1$ and/or $R^2$ may occasionally be of importance due to better solubility in the customary liquid-crystalline base materials, but in particular as chiral dopes if they are optically active. Smectic compounds of this type are suitable as components for ferroelectric materials.

Branched groups of this type generally contain not more than one chain branch. Preferred branched radicals R and/or $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

The formula I covers the racemates of these compounds and the optical antipodes, and mixtures thereof.

Of these compounds of the formula I and the subformulae, preference is given to those in which at least one of the radicals present therein has one of the preferred meanings indicated.

In the compounds of the formula I, preference is given to the stereoisomers in which the rings Cyc and piperidine are trans-1,4-disubstituted. Those of the abovementioned formulae which contain one or more groups Pyd, Pyr and/or Dio in each case include the two 2,5-positional isomers.

Some very particularly preferred smaller groups of compounds of the formula I are those of the subformulae I152 to I181:

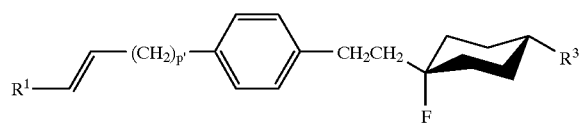

I152

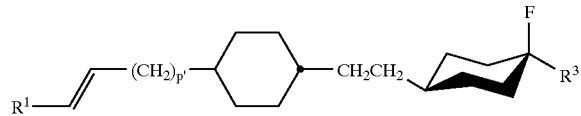

I153

-continued
I154
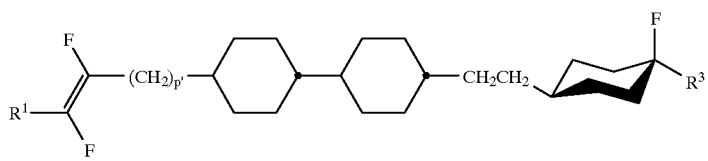
I155
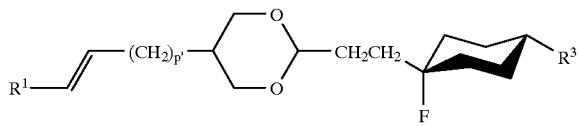
I156
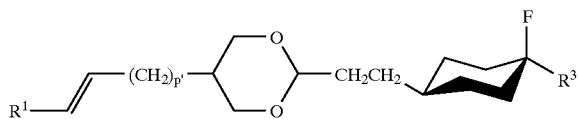
I157
I158
I159
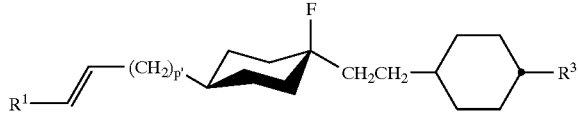
I160
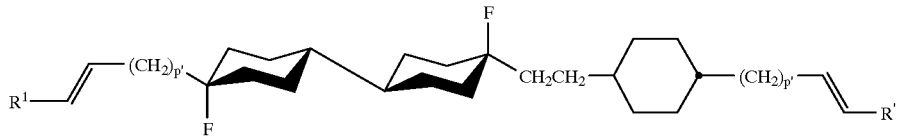
I161
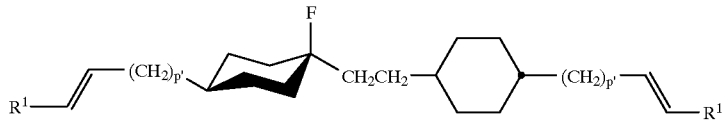
I162
I163
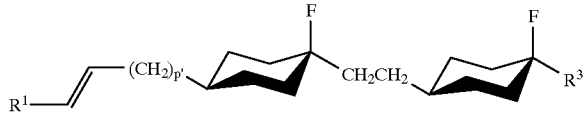
I164
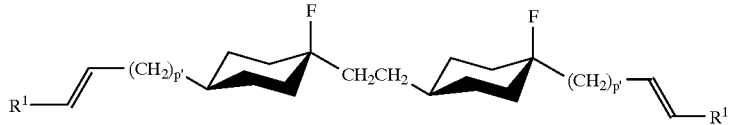

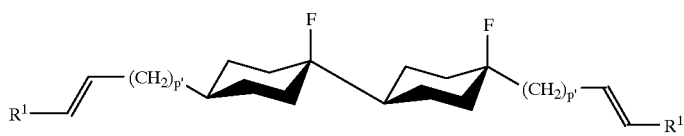 I165
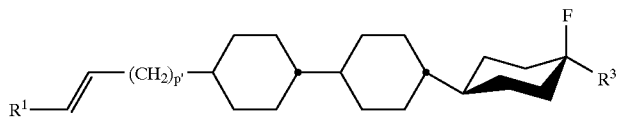 I166
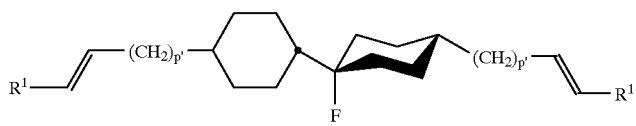 I167
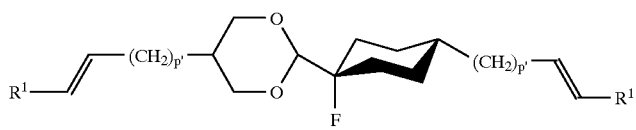 I168
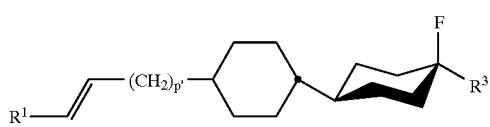 I169
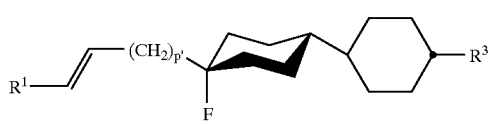 I170
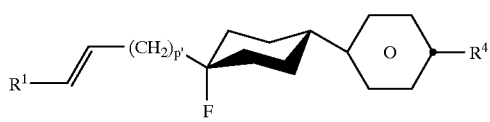 I171
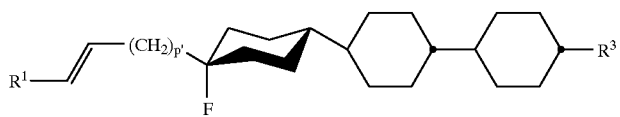 I172
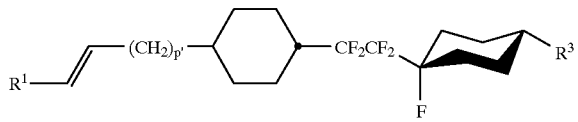 I173
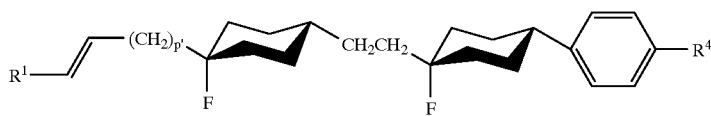 I174
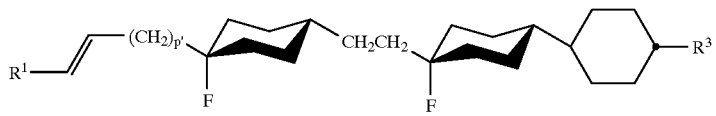 I175

-continued

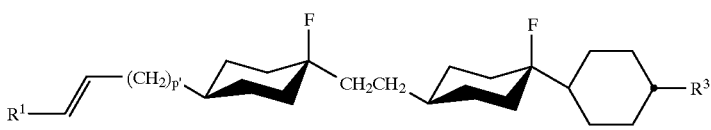
I176

I177

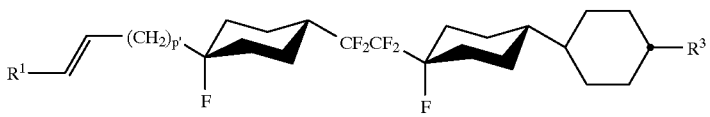
I178

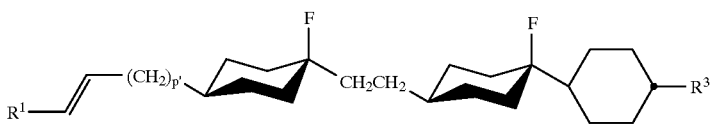
I179

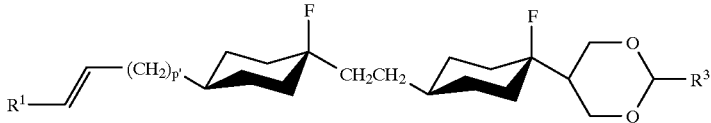
I180

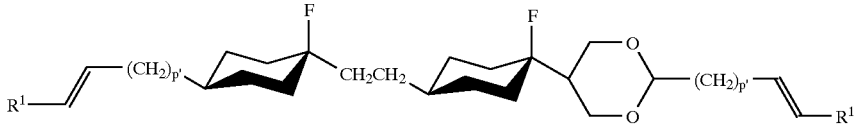
I181 in which $R^1$ is as defined above, p' is 0, 1, 2 or 3, and $R^3$ is straight-chain alkyl or alkoxy having 1 to 6 carbon atoms.

$R^4$ in the abovementioned formulae is CN, F, $CF_3$, $OCF_3$ or straight-chain alkoxy having 1 to 6 carbon atoms.

Very particularly preferred compounds from this group are those of the formulae I153, I156, I158, I160, I161, I162, I164, I165, I169, I170, I171, I176 and I181.

The compounds of the formula I are prepared by methods known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for said reactions.

Use can also be made here of variants which are known per se, but are not described here in greater detail.

The axially fluorinated compounds of the formula I according to the invention can be synthesized by using hydrogen fluoride under pressure or by means of amine/hydrogen fluoride adducts (for example A. V. Grosse, C. B. Linn, J. Org. Chem. 3, (1938) 26; G. A. Olah, M. Nojima, I. Kerekes, Synthesis, (1973), 779; G. A. Olah, X-Y. Li, Q. Wang, G. K. S. Prakash, Synthesis (1993) 693).

The novel compounds can be prepared, for example, in accordance with the following reaction schemes:

Scheme 1

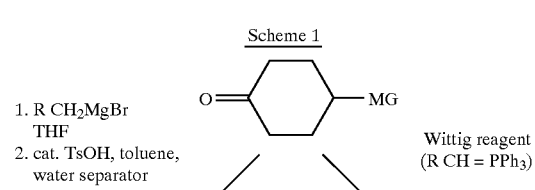

1. R $CH_2MgBr$
   THF
2. cat. TsOH, toluene,
   water separator

Wittig reagent
(R CH = $PPh_3$)

-continued
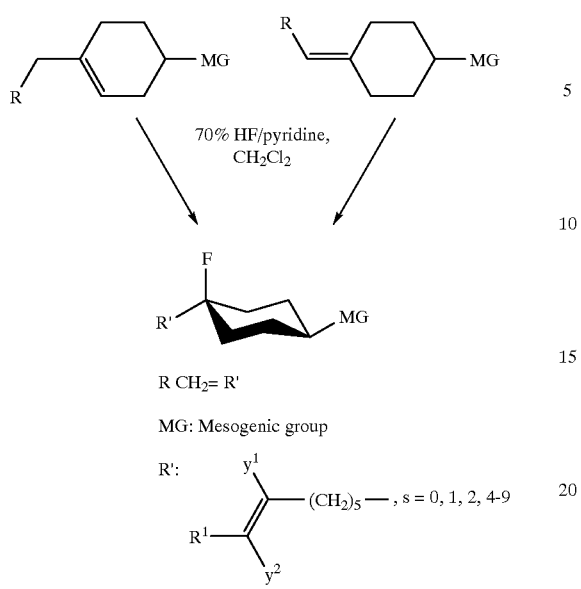
R CH₂= R'
MG: Mesogenic group
R':
$\underset{R^1}{\overset{y^1}{>}}=\underset{y^2}{\overset{}{<}}(CH_2)_5-$, s = 0, 1, 2, 4-9
Scheme 2
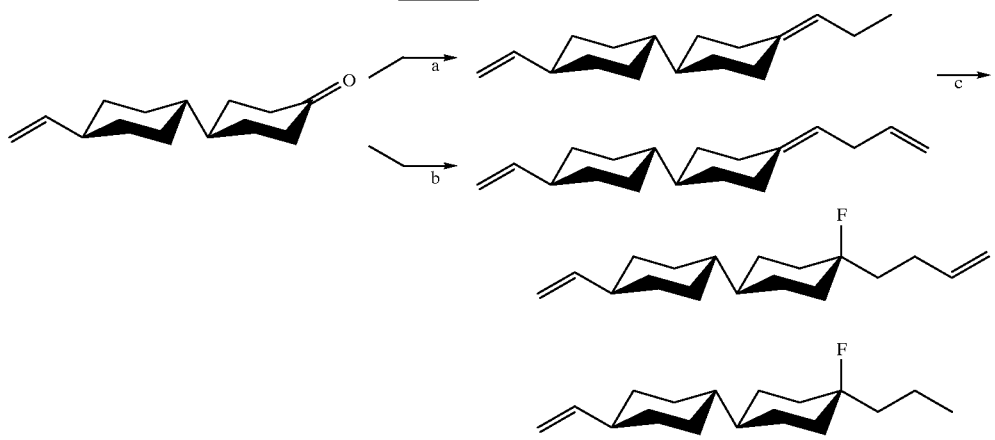
a) H₃CCH₂CH₂PPh₃⁺Br⁻, KOtBu, THF; -10° C. ⟶ RT, 2 h
b) H₂C=CHCH₂CH₂PPh₃⁺Br⁻, KOtBu, THF; -10° C. ⟶ RT, 2 h
c) 4 equivs. 70% HF/pyridine, CH₂Cl₂; -25° C. ⟶ RT, 10 min
Scheme 3
IA

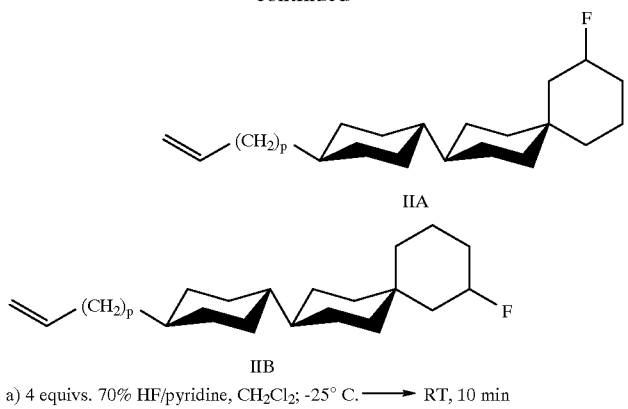

IIA

IIB a) 4 equivs. 70% HF/pyridine, CH$_2$Cl$_2$; -25° C. ⟶ RT, 10 min

The reaction of hydrogen fluoride with pentenyl derivatives of type IA is accompanied by cyclization to the products IIA and IIB, which can be separated by chromatography. They can be used as components of liquid crystalline media and are likewise a subject-matter of the present invention.

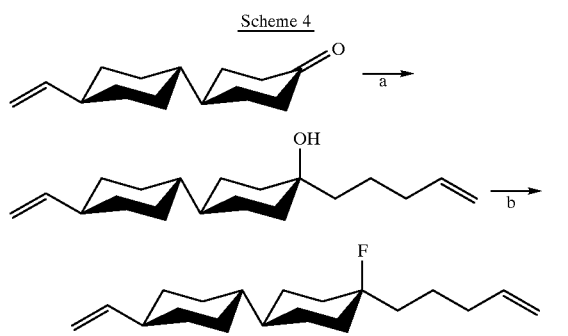

a) BrMg(CH$_2$)$_3$CH═CH$_2$, THF
b) 4 equivs. 70% HF/pyridine, CH$_2$Cl$_2$; -25° C. ⟶ RT, 10 min Scheme 5

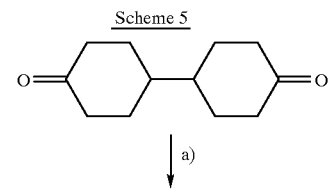

a) H$_2$C═CHCH$_2$CH$_2$PPh$_3$$^+$Br$^-$; KOtBu, THF
b) HF/pyridine, CH$_2$Cl$_2$ Scheme 6

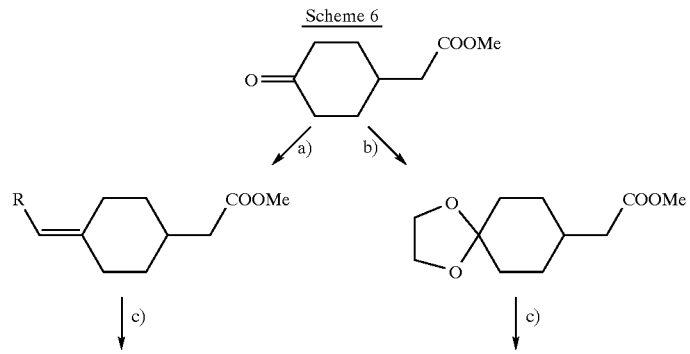

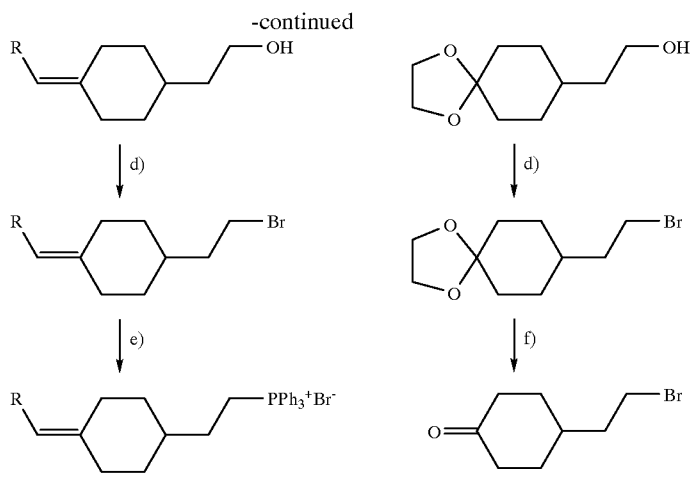
a) R CH$_2$PPh$_3^+$Br$^-$, KOtBu, THF
b) Ethylene glycol, cat. TsOH, toluene
c) LiAlH$_4$, THF
d) PPh$_3$, CBr$_4$, CH$_3$CN
e) PPh$_3$, DMPU
f) HCOOH, toluene
Scheme 7
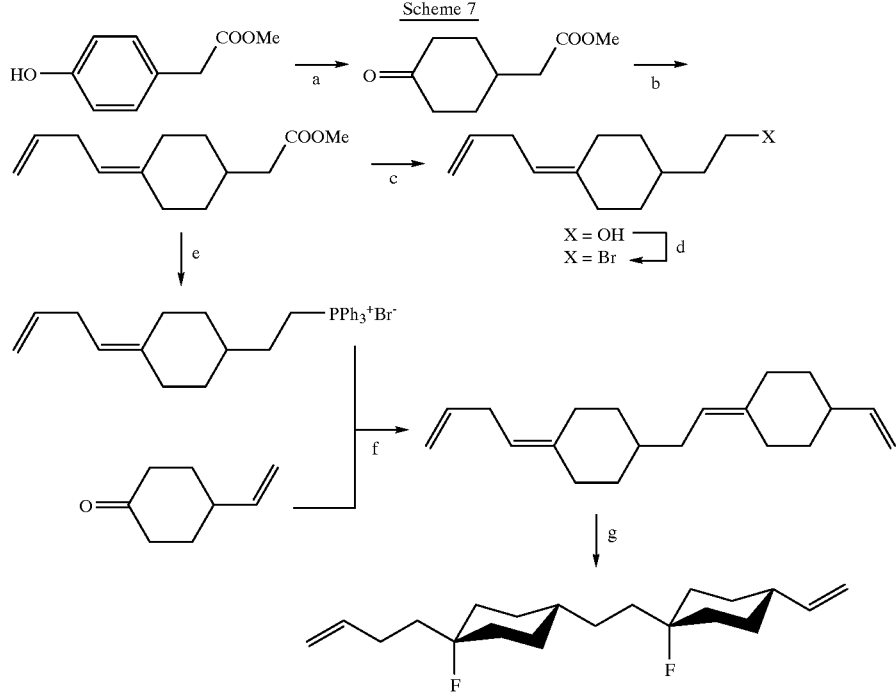
a) H$_2$, 5% Pd/C, toluene
b) H$_2$C═CHCH$_2$CH$_2$PPh$_3^+$Br$^-$, KOtBu; THF; -10° C. ⟶ RT, 2 h
c) LiAlH$_4$, THF; reflux, 3 h
d) CBr$_4$, PPh$_3$, CH$_2$CN; -5° C. ⟶ RT, 18 h
e) PPh$_3$, DMPU; 75° C., 18 h
f) KOtBu, THF; -10° C. ⟶ RT, 2 h
g) 19.5 equivs. 70% HF/pyridine, CH$_2$Cl$_2$; -25° C. ⟶ RT, 10 min

55
Scheme 8
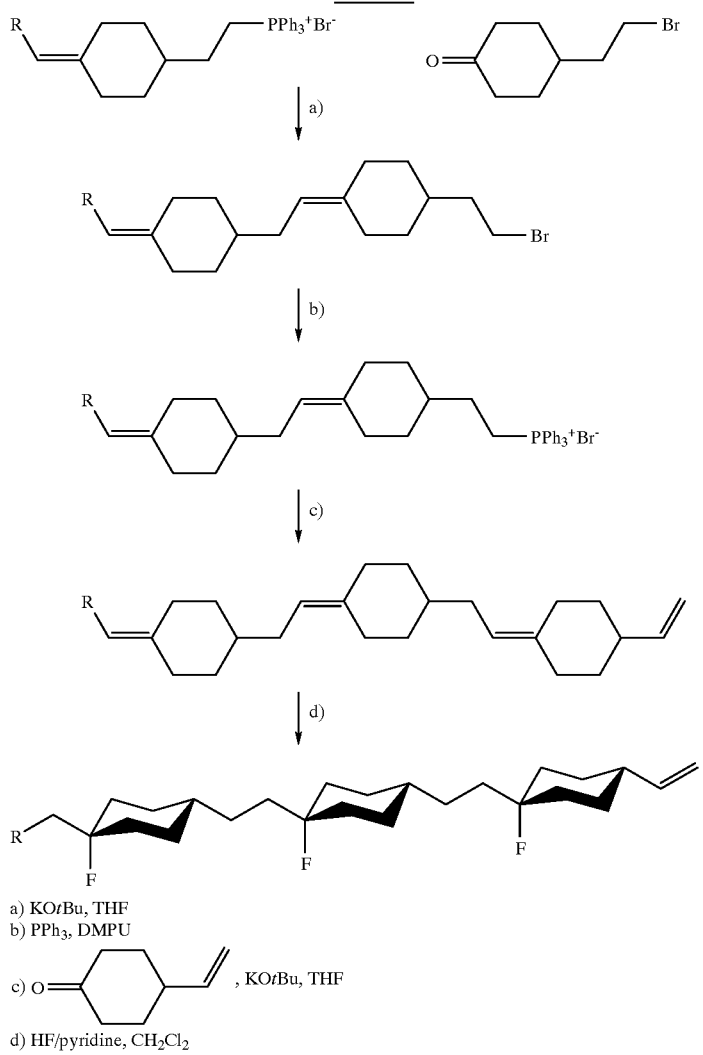
a) KOtBu, THF
b) PPh₃, DMPU
c) <span>O=⬡—CH=CH₂</span>, KOtBu, THF
d) HF/pyridine, CH₂Cl₂
Scheme 9
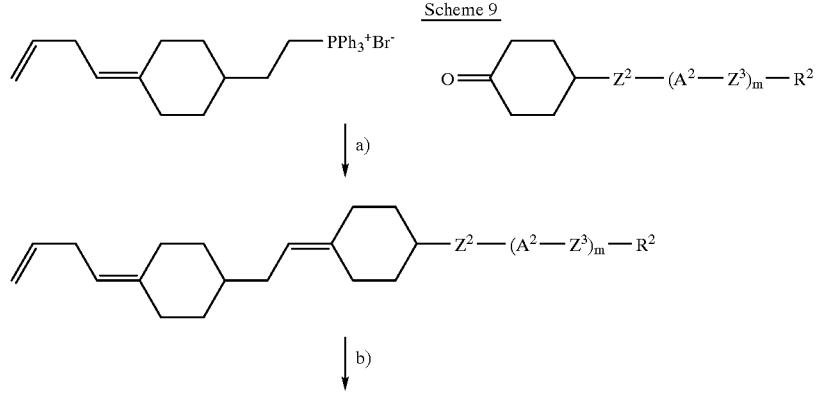

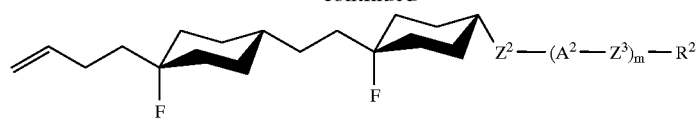
a) KOtBu, THF
b) HF/pyridine, CH$_2$Cl$_2$
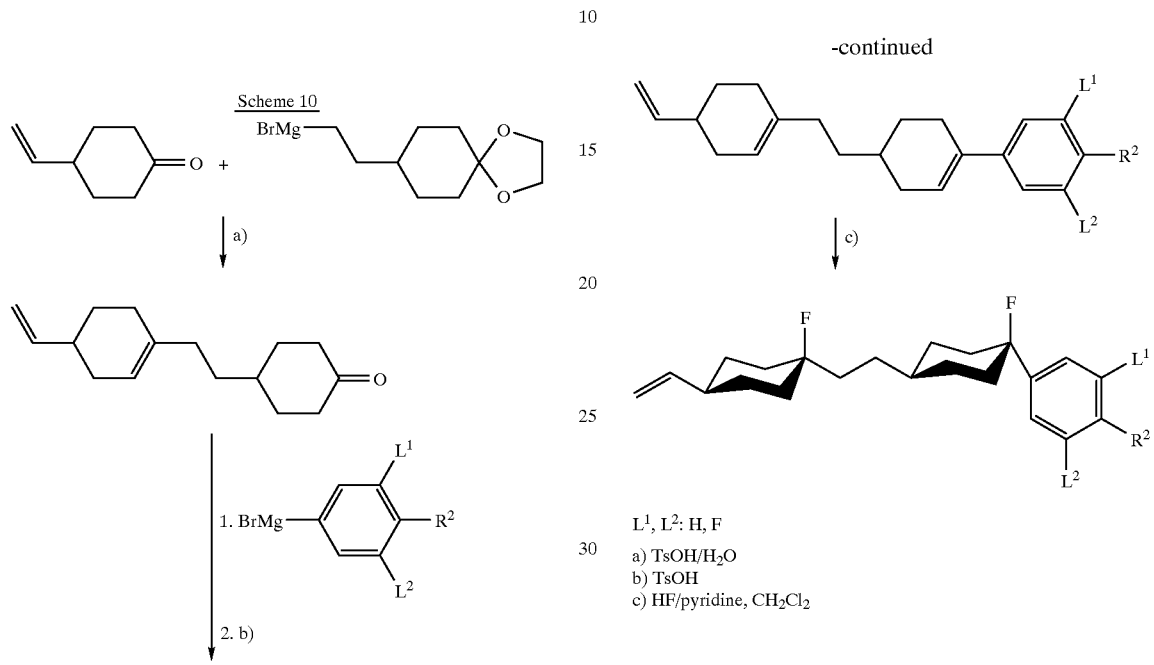
L$^1$, L$^2$: H, F
a) TsOH/H$_2$O
b) TsOH
c) HF/pyridine, CH$_2$Cl$_2$
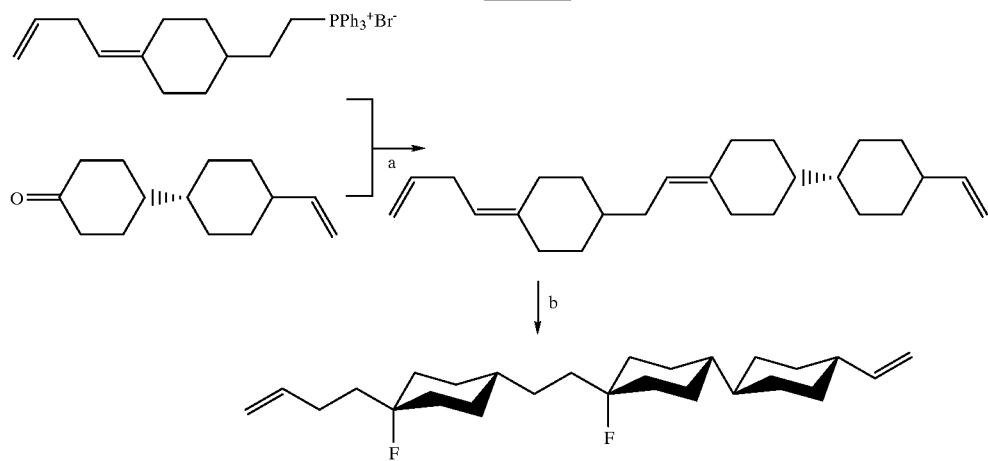
a) KOtBu, THF; -10° C. ⟶ RT, 2 h
b) 4 equivs. 70% HF/pyridine, CH$_2$Cl$_2$; -25° C. ⟶ RT, 10 min Esters of the formula I can also be obtained by esterification of corresponding carboxylic acids (or reactive derivatives thereof) using alcohols or phenols (or reactive derivatives thereof) or by the DCC method (DCC= dicyclohexylcarbodiimide).

The corresponding carboxylic acids and alcohols or phenols are known or can be prepared analogously to known processes.

In a further process for the preparation of compounds of the formula I in which $Z^1, Z^2$ or $Z^3$ is —CH═CH—, an aryl halide is reacted with an olefin in the presence of a tertiary amine and in the presence of a palladium catalyst (cf. R. F. Heck, Acc. Chem. Res. 12 (1979) 146). Examples of suitable aryl halides are chlorides, bromides and iodides, in particular bromides and iodides. The tertiary amines which are necessary for the success of the coupling reaction, such as, for example, triethylamine, are also suitable as solvent.

Examples of suitable palladium catalysts are palladium salts, in particular Pd(II) acetate, and organophosphorous (III) compounds, such as, for example, triaryl-phosphines. Reaction can be carried out in the presence or absence of an inert solvent, at temperatures between 0° C. and 150° C., preferably between 20° C. and 100° C.; examples of suitable solvents are nitriles, such as acetonitrile, or hydrocarbons, such as benzene or toluene. The aryl halides and olefins employed as starting materials are frequently commercially available or can be prepared by processes known from the literature, for example by halogenation of corresponding parent compounds or by elimination reactions on corresponding alcohols or halides.

In this way, for example, stilbene derivatives can be prepared. Stilbenes can furthermore be prepared by reacting a 4-substituted benzaldehyde with a corresponding phosphorous ylide by the Wittig method. However, it is also possible to prepare tolans of the formula I by using monosubstituted acetylene instead of the olefin (Synthesis 627 (1980) or Tetrahedron Lett. 27, 1171 (1986)).

Furthermore, the coupling of aromatic compounds can be carried out by reacting aryl halides with aryltin compounds. These reactions are preferably carried out with addition of a catalyst, such as, for example, a palladium(0) complex, in inert solvents, such as hydrocarbons, at high temperatures, for example in boiling xylene under a protective gas.

Coupling reactions of alkynyl compounds with aryl halides can be carried out analogously to the process described by A. O. King, E. Negishi, F. J. Villani and A. Silveira in J. Org. Chem. 43, 358 (1978).

Tolans of the formula I in which $Z^1$ or $Z^3$ is —C≡C— can also be prepared by Fritsch-Buttenberg-Wiechell rearrangement (Ann. 279, 319, 1984), in which 1,1-diaryl-2-haloethylenes are rearranged in the presence of strong bases to give diarylacetylenes.

Tolans of the formula I can also be prepared by brominating the corresponding stilbenes, and then subjecting the products to dehydrohalogenation. Use can also be made here of variants of this reaction which are known per se, but are not mentioned here in greater detail.

Ethers of the formula I are obtainable by esterification of corresponding hydroxyl compounds, preferably corresponding phenols, where the hydroxyl compound is advantageously first converted into a corresponding metal derivative, for example into the corresponding alkali metal alkoxide or alkali metal phenoxide by treatment with NaH, NaNH$_2$, NaOH, KOH, Na$_2$CO$_3$ or K$_2$CO$_3$. This alkoxide or phenoxide can then be reacted with the appropriate alkyl halide, alkyl sulphonate or dialkyl sulphate, advantageously in an inert solvent, such as, for example, acetone, 1,2-dimethoxyethane, DMF or dimethyl sulphoxide, or alternatively with an excess of aqueous or aqueous-alcoholic NaOH or KOH, at temperatures between about 20° C. and 100° C.

The starting materials are either known or can be prepared analogously to known compounds.

The liquid-crystalline media according to the invention preferably comprise from 2 to 40, in particular from 4 to 30, components as further constituents besides one or more compounds according to the invention. These media very particularly preferably comprise from 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl) ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—CH$_2$CH$_2$—E—R" | 4 |
| R'—L—C≡C—E—R" | 5 |

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-,-Dio-, -G-Phe- and -G-Cyc- and their mirror images, where Phe is unsubstituted or fluorine-substituted 1,4-phenylene, Cyc is trans-1,4-cyclohexylene or 1,4-cyclo-hexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

In a smaller sub-group of the compounds of the formulae 1, 2, 3, 4 and 5, R' and R" are in each case, independently of one another, alkyl, alkenyl, alkoxy, alkoxyalkyl, alkenyloxy or alkanoyloxy having up to 8 carbon atoms. This smaller sub-group is called group A below, and the compounds are labeled with the subformulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5 which is known as group B, R" is —F, —Cl, —NCS or —(O)$_i$CH$_{3-(k+l)}$F$_k$Cl$_l$, where i is 0 or 1, and k and l are 1, 2 or 3; the compounds in which R" has this meaning are labeled with the sub-formulae 1b, 2b, 3b, 4b and 5b. Particular preference is given to those compounds of the sub-formulae 1b, 2b, 3b, 4b and 5b which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and S, R"is —CN; this sub-group is known as group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. A$^1$ these substances can be obtained by methods which are known from the literature or analogously thereto.

Besides compounds of the formula I according to the invention, the media according to the invention preferably comprise one or more compounds selected from group A and/or group B and/or group C. The proportions by weight of the compounds from these groups in the media according to the invention are preferably Group A: from 0 to 90%, preferably from 20 to 90%, in particular from 30 to 90%

Group B: from 0 to 80%, preferably from 10 to 80%, in particular from 10 to 65%

Group C: from 0 to 80%, preferably from 5 to 80%, in particular from 5 to 50%, the sum of the proportions by weight of the group A and/or B and/or C compounds present in the particular media according to the invention preferably being 5%-90% and in particular from 0% to 90%.

The media according to the invention preferably comprise from 1 to 40%, particularly preferably from 5 to 30%, of compounds according to the invention. Further preferred media are those which comprise more than 40%, in particular from 45 to 90%, of compounds according to the invention. The media preferably comprise three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

The examples below are intended to illustrate the invention without representing a limitation. Above and below, percent data are percent by weight. All temperatures are given in degrees Celsius. m.p.=melting point, cl.p.=clearing point. Furthermore, C=crystalline state, N=nematic phase, S=smectic phase and I=isotropic phase. The number between two symbols indicates the conversion temperature in degrees Celsius. Δn denotes optical anisotropy (589 nm, 20° C.) and Δε the dielectric anisotropy (1 kHz, 20° C.). The viscosity (mm$^2$/sec) was determined at 20° C.

"Conventional work-up" means that water is added if necessary, the mixture is extracted with methylene chloride, diethyl ether, or toluene, the organic phase is separated off, dried and evaporated, and the product is purified by distillation under reduced pressure or crystallization and/or chromatography.

The following abbreviations are used:

| | |
|---|---|
| THF | tetrahydrofuran |
| KOtBu | potassium tert-butoxide |
| RT | room temperature |

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application No. 197 32 772.9, filed Jul. 30, 1997 is hereby incorporated by reference.

EXAMPLE 1

4'-But-3-enylidene-4-vinylbicyclohexyl 20.6 g of 4'-vinylbicyclohexyl-4-one and 39.7 g of triphenyl(3-butenyl)phosphonium bromide in 250 ml of THF were cooled to −10° C. under nitrogen with stirring. A solution of 11.44 g of potassium tert-butoxide in 150 ml of THF was then added dropwise at −10° C. with stirring, and the mixture was then stirred at RT for a further 2 hours. The yellow suspension was cooled to 10° C., and 500 ml of water were added. The organic phase was separated off, and the aqueous phase was extracted once with 100 ml of methyl tert-butyl ether. Combined organic extracts were washed once with 100 ml of water, dried using sodium sulfate, filtered and evaporated to give a residue, giving 4'-but-3-enylidene-4-vinylbicyclohexyl.

EXAMPLE 2

4-But-3-enyl-4-fluoro-4'-vinylbicyclohexyl 20.6 g of 4'-but-3-enylidene-4-vinylbicyclohexyl in 40 ml of dichloromethane were cooled to −25° C. 7.523 ml of a 70% solution of hydrogen fluoride in pyridine were then added dropwise with stirring, and the mixture was stirred at −25° C. for 30 minutes and then at RT for a further 8 hours.

The reaction solution was poured into a suspension of 40 g of sodium hydrogencarbonate and 800 g of ice-water. The mixture was extracted with three times 150 ml of hexane. The combined organic extracts were washed once with 50 ml of sodium chloride solution, dried using sodium sulphate, filtered and evaporated to a residue. Crystallization from pentane at −25° C. gave 4-but-3-enyl-4-fluoro-4'-vinylbicyclohexyl (C 13 SmB 37 N 80 I, Δn=0.049, Δε=−1.8, viscosity=13 mm$^2$).

The following compounds according to the invention are obtained analogously from the corresponding precursors:

EXAMPLES 3–39

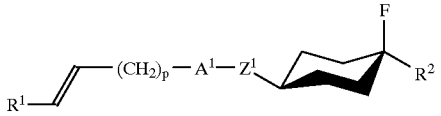

| | p | R$^1$ | A$^1$ | Z$^1$ | R$^2$ |
|---|---|---|---|---|---|
| (3) | 1 | H |  | CH$_2$CH$_2$ | n-Propyl |
| (4) | 3 | H | 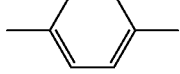 | CH$_2$CH$_2$ | n-Pentyl |
| (5) | 1 | Ethyl |  | CH$_2$CH$_2$ | n-Propyl |
| (6) | 1 | H | 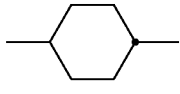 | CH$_2$CH$_2$ | n-Propyl |
| (7) | 2 | H |  | CH$_2$CH$_2$ | n-Propyl |
| (8) | 5 | H | 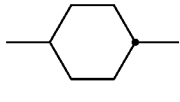 | CH$_2$CH$_2$ | n-Pentyl |
| (9) | 1 | CH$_3$ | 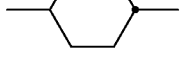 | CH$_2$CH$_2$ | n-Propyl |
| (10) | 2 | CH$_3$ |  | CH$_2$CH$_2$ | n-Pentyl |
| (11) | 0 | H | 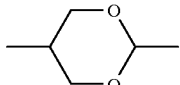 | CH$_2$CH$_2$ | n-Propyl |
| (12) | 2 | H | 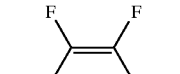 | CH$_2$CH$_2$ | n-Butyl |

-continued
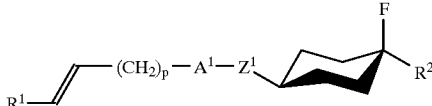
| | p | R¹ | A¹ | Z¹ | R² | |
|---|---|---|---|---|---|---|
| (13) | 3 | H | 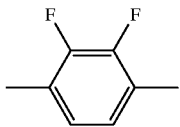 | CH₂CH₂ | n-Pentyl | |
| (14) | 3 | CH₃ | 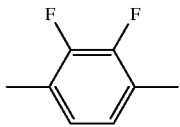 | CH₂CH₂ | n-Propyl | |
| (15) | 1 | H |  | — | n-Propyl | |
| (16) | 0 | H |  | — | Ethyl | (C −29 SmB 49 I Δn: 0.024, Δε: −1.5) |
| (17) | 0 | H |  | — | n-Propyl | (C 29 SmB 58 N 69 I Δn: 0.053, Δε: −1.7) |
| (18) | 0 | H |  | — | n-Butyl | C 18 SmB 77 I, Δn: 0.039, Δε: −1.8) |
| (19) | 0 | H |  | — | n-Pentyl | C 26 SmB 80 N 81 I, Δn: 0.045, Δε: −1.6) |
| (20) | 3 | H |  | — | trans-CH₂CH=CHCH₃ | |
| (21) | 3 | Ethyl | 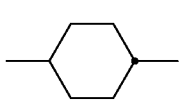 | — | n-Heptyl | |
| (22) | 1 | H | 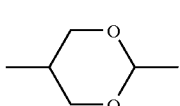 | — | n-Propyl | |
| (23) | 2 | H | 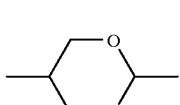 | — | n-Propyl | |
| (24) | 3 | H | 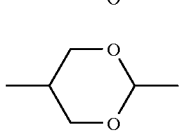 | — | n-Propyl | |

-continued
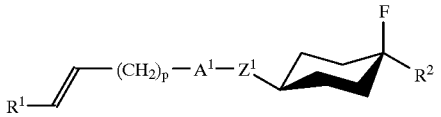
| | p | R¹ | A¹ | Z¹ | R² |
|---|---|---|---|---|---|
| (25) | 1 | H | 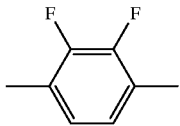 | — | n-Butyl |
| (26) | 2 | H | 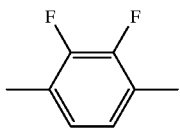 | — | n-Propyl |
| (27) | 3 | H | 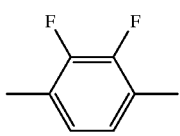 | — | n-Propyl |
| (28) | 3 | CH₃ | 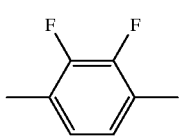 | — | n-Propyl |
| (29) | 1 | H | 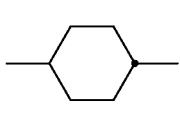 | — | O-n-Propyl |
| (30) | 2 | H | 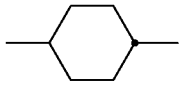 | — | O-n-Pentyl |
| (31) | 2 | CH₃ |  | CH₂CH₂ | O-n-Pentyl |
| (32) | 1 | CH₃ |  | — | O-n-Pentyl |
| (33) | 2 | CH₃ |  | — | O-n-Pentyl |
| (34) | 1 | CH₃ | 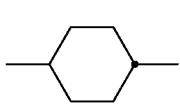 | — | O-n-Pentyl |

-continued

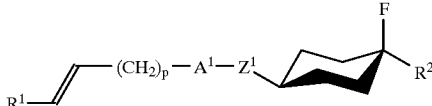

| | p | R¹ | A¹ | Z¹ | R² |
|---|---|---|---|---|---|
| (35) | 4 | H | (1,4-phenylene) | CH₂CH₂ | CH₂CH=CH₂ |
| (36) | 1 | H | (trans-1,4-cyclohexylene) | CH₂CH₂ | OCH₂CH=CH₂ |
| (37) | 2 | H | (trans-1,4-cyclohexylene) | CH₂CH₂ | CH=CH₂ |
| (38) | 1 | H | (trans-1,4-cyclohexylene) | — | trans-CH₂CH=CHCH₃ |
| (39) | 2 | H | (trans-1,4-cyclohexylene) | — | CH₂CH=CH₂ |

EXAMPLES 40–55

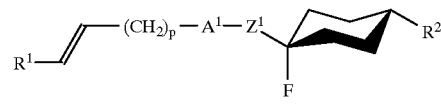

| | p | R¹ | A¹ | Z¹ | R² |
|---|---|---|---|---|---|
| (40) | 3 | H | (trans-1,4-cyclohexylene) | CH₂CH₂ | n-Pentyl |
| (41) | 1 | CH₃ | (trans-1,4-cyclohexylene) | CH₂CH₂ | n-Propyl |
| (42) | 1 | H | (1,3-dioxane-2,5-diyl) | CH₂CH₂ | n-Propyl |
| (43) | 3 | CH₃ | (2,3-difluoro-1,4-phenylene) | CH₂CH₂ | n-Propyl |

-continued
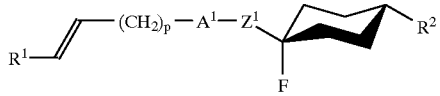
| | p | R¹ | A¹ | Z¹ | R² |
|---|---|---|---|---|---|
| (44) | 2 | H | 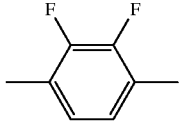 | — | n-Propyl |
| (45) | 2 | H | | — | n-Pentyl |
| (46) | 0 | H | | — | trans-CH₂CH=CHCH₃ |
| (47) | 0 | H | | — | n-Propyl |
| (48) | 1 | H | 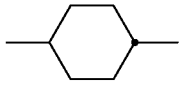 | — | n-Propyl |
| (49) | 1 | H | 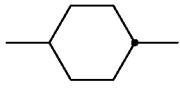 | — | n-Butyl |
| (50) | 1 | H | | — | O-n-Propyl |
| (51) | 4 | H | | — | O-n-Pentyl |
| (52) | 1 | H | | CH₂CH₂ | OCH₂CH=CH₂ |
| (53) | 2 | H | | CH₂CH₂ | CH=CH₂ |
| (54) | 1 | H | | — | CH₂CH=CH₂ |
| (55) | 2 | H | | — | CH₂CH=CH₂ |

EXAMPLES 56–71

[Structure: R¹–CH=CH–(CH₂)ₚ–A¹–Z¹–[cyclohexyl with F]–[cyclohexyl with F]–R²]

| | p | R¹ | A¹ | Z¹ | R² |
|---|---|---|---|---|---|
| (56) | 3 | H | cyclohexyl | CH₂CH₂ | n-Pentyl |
| (57) | 1 | CH₃ | cyclohexyl | CH₂CH₂ | n-Propyl |
| (58) | 1 | H | 1,3-dioxane | CH₂CH₂ | n-Propyl |
| (59) | 3 | CH₃ | 2,3-difluorophenyl | CH₂CH₂ | n-Propyl |
| (60) | 1 | H | cyclohexyl | — | n-Propyl |
| (61) | 0 | H | cyclohexyl | — | n-Pentyl |
| (62) | 3 | H | cyclohexyl | — | trans-CH₂CH=CHCH₃ |
| (63) | 1 | CH₃ | cyclohexyl | — | — |
| (64) | 1 | H | 1,3-dioxane | — | n-Propyl |
| (65) | 1 | H | 2,3-difluorophenyl | — | n-Butyl |
| (66) | 1 | H | cyclohexyl | — | O-n-Propyl |

-continued
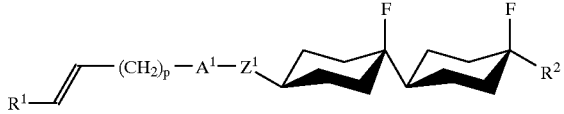
| | p | R¹ | A¹ | Z¹ | R² |
|---|---|---|---|---|---|
| (67) | 2 | H |  | — | O-n-Pentyl |
| (68) | 1 | H |  | CH₂CH₂ | OCH₂CH=CH₂ |
| (69) | 2 | H | — | — | CH=CH₂ |
| (70) | 1 | H | — | — | CH₂CH=CH₂ |
| (71) | 2 | H |  | — | CH₂CH=CH₂ |
EXAMPLES 72–87
| | p | R¹ | A¹ | Z¹ | R² |
|---|---|---|---|---|---|
| (72) | 3 | H |  | CH₂CH₂ | n-Pentyl |
| (73) | 1 | CH₃ |  | CH₂CH₂ | n-Propyl |
| (74) | 1 | H | 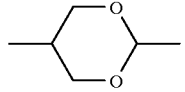 | CH₂CH₂ | n-Propyl |
| (75) | 3 | CH₃ | 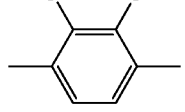 | CH₂CH₂ | n-Propyl |
| (76) | 1 | H |  | — | n-Propyl |
| (77) | 0 | H | 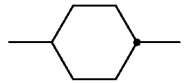 | — | n-Pentyl |

-continued $$R^1\text{—}\overset{}{=}\text{—}(CH_2)_p\text{—}A^1\text{—}Z^1\text{—}\underset{F}{\text{Cy}}\text{—}CH_2CH_2\text{—}\underset{F}{\text{Cy}}\text{—}R^2$$

| | p | R¹ | A¹ | Z¹ | R² |
|---|---|---|---|---|---|
| (78) | 2 | H | (cyclohexyl) | — | trans-CH₂CH=CHCH₃ |
| (79) | 1 | Ethyl | — | — | n-Propyl |
| (80) | 1 | H | (1,3-dioxane) | — | n-Propyl |
| (81) | 1 | H | (2,3-difluorophenyl) | — | n-Butyl |
| (82) | 1 | H | (cyclohexyl) | — | O-n-Propyl |
| (83) | 2 | H | (cyclohexyl) | — | O-n-Pentyl |
| (84) | 1 | H | (cyclohexyl) | CH₂CH₂ | OCH₂CH=CH₂ |
| (85) | 2 | H | — | — | CH=CH₂ |
| (86) | 0 | H | (cyclohexyl) | — | CH₂CH=CH₂ |
| (87) | 2 | H | (cyclohexyl) | — | CH₂CH=CH₂ |

EXAMPLES 88–132

$$R^1\text{—}\overset{}{=}\text{—}(CH_2)_p\text{—}\underset{F}{\text{Cy}}\text{—}Z^2\text{—}A^2\text{—}R^2$$

| | p | R¹ | Z² | A² | R² |
|---|---|---|---|---|---|
| (88) | 1 | H | CH₂CH₂ | (phenyl) | n-Pentyl |

-continued
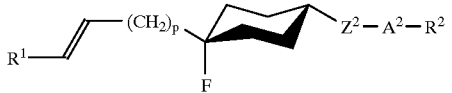
| | p | R₁ | Z² | A² | R² | |
|---|---|---|---|---|---|---|
| (89) | 3 | $CH_3$ | $CH_2CH_2$ |  | n-Propyl | |
| (90) | 1 | H | $CH_2CH_2$ |  | n-Pentyl | |
| (91) | 2 | H | $CH_2CH_2$ |  | n-Propyl | (m.p.: 37, Δn: 0.051, Δε: −1.4) |
| (92) | 2 | H | — |  | n-Propyl | (C 48 SmB 95 N 102 I, Δn: 0.059, Δε: −1.61) |
| (93) | 0 | H | — |  | n-Propyl | (C 29 SmB 55 I Δn: 0.043, Δε: −0.92) |
| (94) | 1 | Ethyl | — | 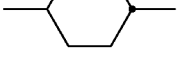 | n-Pentyl | |
| (95) | 2 | H | $CH_2CH_2$ | 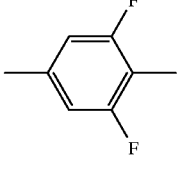 | n-Propyl | |
| (96) | 5 | H | — | 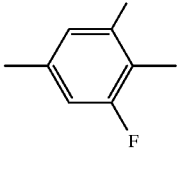 | n-Pentyl | |
| (97) | 3 | $CH_3$ | — | 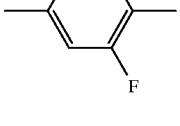 | n-Pentyl | |

-continued
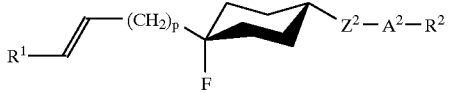
| | p | R¹ | Z² | A² | R² |
|---|---|---|---|---|---|
| (98) | 1 | H | CH₂CH₂ |  | O-n-Propyl |
| (99) | 2 | H | CH₂CH₂ |  | O-n-Propyl |
| (100) | 0 | H | CH₂CH₂ |  | O-n-Propyl |
| (101) | 1 | CH₃ | CH₂CH₂ | 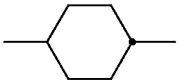 | O-n-Propyl |
| (102) | 3 | H | — |  | O-n-Propyl |
| (103) | 1 | CH₃ | — | 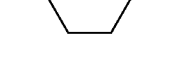 | O-n-Propyl |
| (104) | 1 | CH₃ | CH₂CH₂ | 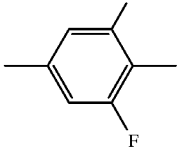 | O-n-Propyl |
| (105) | 3 | CH₃ | — | 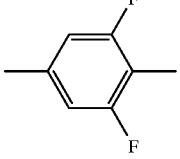 | O-n-Propyl |
| (106) | 1 | H | CH₂CH₂ |  | O-n-Pentyl |
| (107) | 2 | H | CH₂CH₂ |  | O-n-Pentyl |

-continued $$R^1 \diagdown \hspace{-0.3em} = \hspace{-0.3em} \diagup (CH_2)_p - \underset{F}{\overset{}{\diagup\!\!\!\diagdown}} - Z^2 - A^2 - R^2$$

| | p | R₁ | Z² | A² | R² |
|---|---|---|---|---|---|
| (108) | 3 | CH₃ | CH₂CH₂ | cyclohexyl | O-n-Pentyl |
| (109) | 3 | CH₃ | CH₂CH₂ | 3,5-difluorophenyl | O-n-Pentyl |
| (110) | 1 | H | CH₂CH₂ | phenyl | trans-CH₂CH=CHCH₃ |
| (111) | 2 | H | CH₂CH₂ | phenyl | trans-CH₂CH=CHCH₃ |
| (112) | 3 | H | CH₂CH₂ | phenyl | trans-CH₂CH=CHCH₃ |
| (113) | 1 | H | CH₂CH₂ | cyclohexyl | CH₂CH=CH₂ |
| (114) | 2 | H | CH₂CH₂ | cyclohexyl | CH=CH₂ |
| (115) | 1 | CH₃ | CH₂CH₂ | cyclohexyl | trans-CH₂CH=CHCH₃ |
| (116) | 3 | CH₃ | CH₂CH₂ | cyclohexyl | trans-CH₂CH=CHCH₃ |
| (117) | 1 | H | — | cyclohexyl | CH₂CH=CH₂ |

-continued $$R^1 \diagdown (CH_2)_p \diagdown \diagup Z^2-A^2-R^2$$
$$F$$

| | p | R¹ | Z² | A² | R² |
|---|---|---|---|---|---|
| (118) | 2 | H | — | (cyclohexyl) | $CH_2CH{=}CH_2$ |
| (119) | 1 | $CH_3$ | — | (cyclohexyl) | trans-$OCH_2CH{=}CHCH_3$ |
| (120) | 3 | $CH_3$ | — | (cyclohexyl) | $OCH_2CH{=}CH_2$ |
| (121) | 2 | H | $CH_2CH_2$ | (2,3-difluorophenyl) | $CH{=}CH_2$ |
| (122) | 3 | H | $CH_2CH_2$ | (phenyl) | $OCF_3$ |
| (123) | 1 | H | $CH_2CH_2$ | (2,3-difluorophenyl) | $OCF_3$ |
| (124) | 3 | $CH_3$ | $CH_2CH_2$ | (2,3-difluorophenyl) | $OCF_3$ |
| (125) | 2 | $CH_3$ | $CH_2CH_2$ | (phenyl) | CN |

-continued
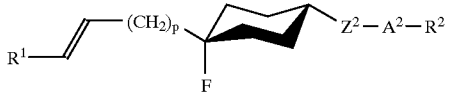
| | p | R₁ | Z² | A² | R² |
|---|---|---|---|---|---|
| (126) | 3 | H | CH₂CH₂ | 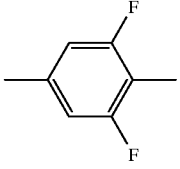 | CN |
| (127) | 3 | H | CH₂CH₂ |  | F |
| (128) | 1 | CH₃ | CH₂CH₂ |  | F |
| (129) | 1 | H | CH₂CH₂ | 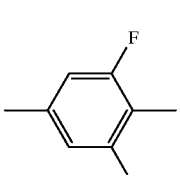 | F |
| (130) | 2 | H | — | 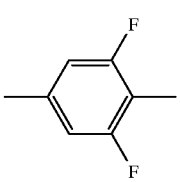 | F |
| (131) | 3 | H | — | 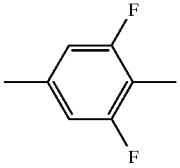 | F |
| (132) | 2 | CH₃ | — | 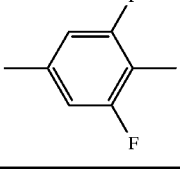 | F |

EXAMPLES 133–149
| | p | R¹ | Z² | A² | R² |
|---|---|---|---|---|---|
| (133) | 1 | H | $CH_2CH_2$ |  | n-Pentyl |
| (134) | 1 | H | — | — | n-Pentyl |
| (135) | 1 | H | — | — | O-n-Propyl |
| (136) | 2 | H | $CH_2CH_2$ |  | O-n-Propyl |
| (137) | 3 | H | $CH_2CH_2$ |  | trans-$CH_2CH=CHCH_3$ |
| (138) | 0 | H | $CH_2CH_2$ |  | trans-$CH_2CH=CHCH_3$ |
| (139) | 1 | $CH_3$ | $CH_2CH_2$ | 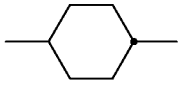 | trans-$CH_2CH=CHCH_3$ |
| (140) | 1 | $CH_3$ | — | — | trans-$CH_2CH=CHCH_3$ |
| (141) | 1 | H | — | — | trans-$CH_2CH=CHCH_3$ |
| (142) | 3 | $CH_3$ | — | 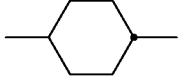 | trans-$CH_2CH=CHCH_3$ |
| (143) | 3 | H | $CH_2CH_2$ | 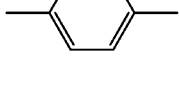 | $OCF_3$ |
| (144) | 1 | H | $CH_2CH_2$ | 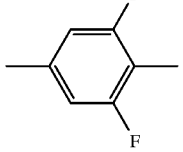 | $OCF_3$ |
| (145) | 2 | $CH_3$ | $CH_2CH_2$ |  | CN |

-continued
| | p | R¹ | Z² | A² | R² |
|---|---|---|---|---|---|
| (146) | 1 | CH₃ | CH₂CH₂ |  | F |
| (147) | 1 | H | CH₂CH₂ | 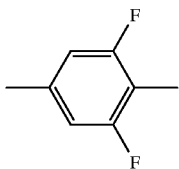 | F |
| (148) | 2 | H | — | 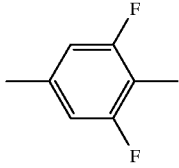 | F |
| (149) | 3 | H | — | 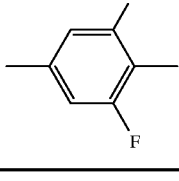 | F |
EXAMPLES 150–166
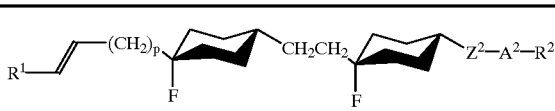
| | p | R¹ | Z² | A² | R² | |
|---|---|---|---|---|---|---|
| (150) | 1 | H | CH₂CH₂ | 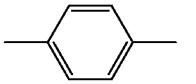 | n-Pentyl | |
| (151) | 1 | H | — | — | n-Pentyl | |
| (152) | 2 | H | — | — | CH=CH₂ | (C 74 SmB (70) N 83 I, Δn: 0.051, Δε: −3.6) |
| (153) | 2 | H | CH₂CH₂ | 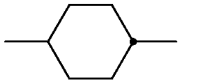 | O-n-Propyl | |

-continued
| | p | R¹ | Z² | A² | R² |
|---|---|---|---|---|---|
| (154) | 3 | H | CH₂CH₂ |  | trans-CH₂CH=CHCH₃ |
| (155) | 0 | H | CH₂CH₂ |  | trans-CH₂CH=CHCH₃ |
| (156) | 1 | CH₃ | CH₂CH₂ | 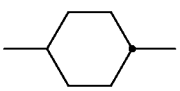 | CH=CH₂ |
| (157) | 3 | CH₃ | CH₂CH₂ |  | trans-CH₂CH=CHCH₃ |
| (158) | 2 | H | — |  | CH=CH₂ |
| (159) | 1 | CH₃ | — | — | trans-CH₂CH=CHCH₃ |
| (160) | 3 | H | CH₂CH₂ |  | OCF₃ |
| (161) | 1 | H | CH₂CH₂ |  | OCF₃ |
| (162) | 2 | CH₃ | CH₂CH₂ | 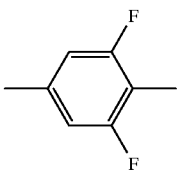 | CN |
| (163) | 1 | CH₃ | CH₂CH₂ |  | F |

-continued

| | p | R₁ | Z² | A² | R² |
|---|---|---|---|---|---|
| (164) | 1 | H | CH₂CH₂ | (3,4,5-trifluorophenyl) | |
| (165) | 2 | H | — | (3,4,5-trifluorophenyl) | |
| (166) | 3 | H | — | (3,4,5-trifluorophenyl) | |

EXAMPLES 167–170

| | p | R₁ | Z¹ | R² |
|---|---|---|---|---|
| (167) | 1 | H | CH₂CH₂ | n-Pentyl |
| (168) | 2 | Me | — | n-Pentyl |
| (169) | 1 | H | — | CH₂CH=CH₂ |
| (170) | 3 | H | CH₂CH₂ | O-n-Propyl |

EXAMPLES 171–173

| | p | R¹ | Z² | R² |
|---|---|---|---|---|
| (171) | 1 | H | CH₂CH₂ | n-Pentyl |
| (172) | 1 | H | — | n-Pentyl |
| (173) | 3 | H | — | CH₂CH=CH₂ |

From the foregoing description, one skilled in the art can easily ascertain the essential characteristics of this invention and, without departing from the spirit and scope thereof, can make various changes and modifications of the invention to adapt it to various usages and conditions.

We claim:
1. A fluorocyclohexane compound of the formula I in which $R^1$ is H, F, or an alkyl, alkoxy or alkenyl radical having 1–12 or 2–12 carbon atoms respectively which is unsubstituted, monosubstituted by CN or $CF_3$ or at least monosubstituted by fluorine, $R^2$ is

, F, CN, an alkyl radical having 1–12 carbon atoms which is unsubstituted, monosubstituted by CN or $CF_3$ or at least monosubstituted by fluorine, where one or more non-adjacent $CH_2$ groups in this radical are optionally, in each case independently of one another, replaced by —O—, —S—, —CO—,

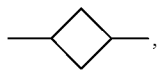

—CO—O—, —O—CO— or —O—CO—O—, $y^1$ and $y^2$, independently of one another, are H or F, $X^1$ and $X^2$ are each, independently of one another, H or F in the axial position, where one of the radicals $X^1$ and $X^2$ on each individual cyclohexane ring substituted by $X^1$ and $X^2$ is F and the other radical is H, $A^1$ and $A^2$ a) are a trans-1,4-cyclohexylene radical, in which, in addition, one or more non-adjacent $CH_2$ groups are optionally replaced by —O— and/or —S—, b) is a 1,4-phenylene radical, in which, in addition, one or two CH groups are optionally replaced by N, c) is a radical selected from the group consisting of 1,4-bicyclo [2.2.2]octylene, piperidine-1,4-diyl, naphthalene-2,6-diyl, decahydronaphthalene-2,6-diyl and 1,2,3,4-tetrahydronaphthalene-2,6-diyl, d) is 1,4-cyclohexenylene, where the radicals a), b) and d) may be substituted by CN, Cl or F, $Z^1$, $Z^2$ and $Z^3$ are each, independently of one another, —CO—O—, —O—CO—, —CH$_2$O—, —O—, —O—CH$_2$—, —CH$_2$CH$_2$—, —CF$_2$CF$_2$—, —CF$_2$CH$_2$—, —CH$_2$CF$_2$—, —CHFCHF—, —CHFCF$_2$—, —CF$_2$CHF—, —CH=CH—, —C≡C— or a single bond, p is 0 to 9, q is 1, 2, 3 or 4, n and m are 0, 1, 2 or 3, where m+n+q is 2, 3 or 4.

2. The fluorocyclohexane compound of the formula I according to claim 1, wherein $Z^1$, $Z^2$ and $Z^3$ are, independently of one another, —CH$_2$CH$_2$—, —CF$_2$CF$_2$—, —CH=CH— or a single bond.

3. The fluorocyclohexane compound of the formula I according to claim 1, wherein the radical $R^2$ is

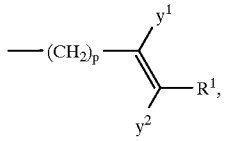

F, —CN, —CF$_3$, —OCF$_3$, —OCHFCF$_3$,

—OCF$_2$CF$_3$, straight-chain alkyl or alkoxy having 1 to 10 carbon atoms or straight-chain fluoroalkyl or fluoroalkoxy having 1 to 10 carbon atoms.

4. The fluorocyclohexane compound of the formula I according to claim 1, wherein p is 0, 1, 2, 3 or 4.

5. The fluorocyclohexane compound of the formula I according to claim 1, wherein $R^1$ is H or straight-chain alkyl having 1 to 3 carbon atoms, and $R^2$ is alkenyl having 2 to 10 carbon atoms.

6. The fluorocyclohexane compound of the formula I according to claim 1, wherein $R^2$ is straight-chain alkyl or alkoxy having 1 to 10 carbon atoms or alkenyl having 2 to 10 carbon atoms, and $A^1$ or $A^2$ is a 1,4-cyclohexylene radical.

7. A liquid-crystalline medium which comprises at least one compound of the formula I of claim 1.

8. A liquid-crystalline medium having at least two liquid-crystalline components, wherein at least one liquid-crystalline component is a compound of the formula I of claim 1.

9. A liquid-crystal display element, which contains a liquid-crystalline medium according to claim 8.

10. An electro-optical display element, which contains, as a dielectric, a liquid-crystalline medium according to claim 8.

11. A compound of the formula IIA

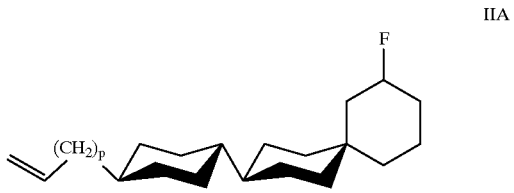

in which p is 0–9.

12. A compound of the formula IIB

in which p is 0–9.

13. An electro-optical display element according to claim 10, for a TFT or STN display.

14. The compound of claim 1, wherein the $A^1$ and $A^2$ groups are independently selected from the group consisting of 1,4-cyclohexylene, 1,4-cyclohexenylene, 1,3-dioxane-2,5-diyl, 1,3-dithiane-2,5-diyl, 1,4-phenylene, pyridine-2,5-diyl, pyrimidine-2,5-diyl, and bicyclo [2.2.2]-octylene radicals wherein the 1,4-cyclohexylene, 1,4-phenylene radicals are optionally substituted by Cl, F or CN.

15. The compound of claim 1, wherein the $A^1$ and $A^2$ groups are independently selected from the group consisting of 1,4-cyclohexylene, 1,3-dioxane-2,5-diyl or 1,4-phenylene which is monosubstituted or disubstituted by F.

16. The medium of claim 7, wherein the medium contains 5–30% by weight of compounds of the formula I.

17. The medium of claim 7, wherein the medium contains more than 40% by weight of compounds of the formula I.

18. The medium of claim 7, wherein the medium comprises three, four or five different compounds of the formula I.

* * * * *